United States Patent
Miranker et al.

(10) Patent No.: US 11,135,213 B2
(45) Date of Patent: Oct. 5, 2021

(54) QUINOLINE AMIDES AND METHODS OF USING SAME

(71) Applicant: YALE UNIVERSITY, New Haven, CT (US)

(72) Inventors: Andrew Miranker, Guilford, CT (US); Sunil Kumar, New York, NY (US)

(73) Assignee: Yale University, New Haven, CT (US)

( * ) Notice: Subject to any disclaimer, the term of this patent is extended or adjusted under 35 U.S.C. 154(b) by 531 days.

(21) Appl. No.: 15/769,914

(22) PCT Filed: Oct. 27, 2016

(86) PCT No.: PCT/US2016/059007
§ 371 (c)(1),
(2) Date: Apr. 20, 2018

(87) PCT Pub. No.: WO2017/075145
PCT Pub. Date: May 4, 2017

(65) Prior Publication Data
US 2020/0246327 A1 Aug. 6, 2020

Related U.S. Application Data

(60) Provisional application No. 62/247,572, filed on Oct. 28, 2015.

(51) Int. Cl.
*A61K 31/4709* (2006.01)
*C07D 401/14* (2006.01)
*A61K 45/06* (2006.01)

(52) U.S. Cl.
CPC .......... *A61K 31/4709* (2013.01); *A61K 45/06* (2013.01); *C07D 401/14* (2013.01)

(58) Field of Classification Search
CPC .. A61K 31/4709; A61K 45/06; C07D 401/14; C07D 215/48; A61P 25/16; A61P 25/28; A61P 3/10
See application file for complete search history.

(56) References Cited

U.S. PATENT DOCUMENTS

2008/0095706 A1  4/2008  Orser et al.

FOREIGN PATENT DOCUMENTS

WO    2005027901 A1    3/2005

OTHER PUBLICATIONS

Christel Dolain, Hua Jiang, Jean-Michel Le' ger, Philippe Guionneau, and Ivan Hue, Chiral Induction in Quinoline-Derived Oligoamide Foldamers: Assignment of Helical Handedness and Role of Steric Effects, J. Am. Chem. Soc. 2005, 127, 12943-12951 (Year: 2005).*
Jérémie Buratto et al., Structure of a Complex Formed by a Protein and a Helical Aromatic Oligoamide Foldamerat 2.1 Å Resolution, Angew. Chem. Int. Ed. 2014, 53, 883-887 (Year: 2014).*
Extended European Search Report for European Patent Application No. 16860752.1 dated Apr. 17, 2019.
Baptiste, et al.,Solid phase synthesis of aromatic oligoamides: application to helical water-soluble foldamers, J Org Chem. 75(21) ,Nov. 2010,7175-7185.
Ferrand, et al.,Diastereoselective encapsulation of tartaric acid by a helical aromatic oligoamide, J Am Chem Soc. 132(23) ,Jun. 2010 ,7858-7859.
Garric, et al.,Encapsulation of small polar guests in molecular apple peels, Chemistry 13(30) ,Oct. 2007 ,8454-8462.
Jiang, et al.,Aromatic δ-peptides: design, synthesis, and structural studies of helical, quinoline-derived oligoamide foldamers, Tetrahedron, 59 ,Oct. 2003 ,8365-8374.
Kumar, et al.,A foldamer approach to targeting membrane bound helical states of islet amyloid polypeptide, Chem Commun (Camb). 49(42) ,May 2013 ,4749-4751.
Kumar, et al.,Foldamer scaffolds suggest distinct structures are associated with alternative gains-of-function in a preamyloid toxin, Chem Commun (Camb). 52(38) ,May 2016 ,6291-6294.
Nguyen, et al.,Low generation anionic dendrimers modulate islet amyloid polypeptide self-assembly and inhibit pancreatic β-cell toxicity, RSC Adv. 6 ,2016 ,76360-76369.
Srinivas, et al.,Remote substituent effects and regioselective enhancement of electrophilic substitutions in helical aromatic oligoamides, J Am Chem Soc.130(40) ,Oct. 2008 ,13210-13211.
International Search Report and Written Opinion for PCT International Application No. PCT/US2016/059007 dated Jan. 13, 2017.
Pubchem CID 16158272, Create Date: Jul. 4, 2007. Date Accessed Dec. 7, 2016 ,p. 3.
Kumar, et al.,Foldamer-mediated manipulation of a pre-amyloid toxin, Nat Commun. 7 ,2016 ,11412.
Kumar, et al.,Folded small molecule manipulation of islet amyloid polypeptide, Chem Biol. 21(6) ,2014 ,775-781.
Hebda, et al.,"A peptidomimetic approach to targeting pre-amyloidogenic states in type II diabetes", Chem Biol. 16(9), 2009, 943-950.

(Continued)

*Primary Examiner* — Sarah Pihonak
*Assistant Examiner* — Jason Deck
(74) *Attorney, Agent, or Firm* — Saul Ewing Arnstein & Lehr LLP; Kathryn Doyle; Domingos J. Silva

(57) ABSTRACT

The present invention provides novel compounds that are quinoline foldamers. Such foldamers stabilize and bind to islet amyloid polypeptide (IAPP). In certain embodiments, the quinoline foldamers of the invention are soluble and cross biological membranes without cellular assistance. The present invention further provides novel method of preventing or treating diabetes in a subject in need thereof by administering to the subject an effective amount of at least one quinoline foldamer of the invention. The present invention further provides novel method of preventing or treating a neurodegenerative disease caused by a misfolded and/or unstructured protein in a subject in need thereof by administering to the subject an effective amount of at least one quinoline foldamer of the invention.

19 Claims, 15 Drawing Sheets
Specification includes a Sequence Listing.

(56) References Cited

OTHER PUBLICATIONS

Kumar, et al.,"Islet amyloid-induced cell death and bilayer integrity loss share a molecular origin targetable with pligopyridylamide-based α-helical mimetics", Chem Biol. 22(3), 2015, 369-378.
Müller, et al.,"Targeting DNA G-Quadruplexes with Helical Small Molecules", Chembiochem. 15(17), 2014, 2563-2570.
Registry (STN) [online], 2014 (Searched Date Sep. 14, 2020), CAS Registered No. 1443829-23-9.
Buratto, et al., "Structure of a complex formed by a protein and a helical aromatic oligoamide foldamer at 2.1 Å resolution", Angew Chem Int Ed Engl. 53(3), Jan. 2014, 883-887.
Kendhale, et al., "Absolute control of helical handedness in quinoline oligoamides", J Org Chem. 76(1), Jan. 2011, 195-200.

* cited by examiner

ADM-116

KCNTATCATQ
RLANFLVHSS
NNFGAILSST
NVGSNTY-NH₂

IAPP

ADM-116I

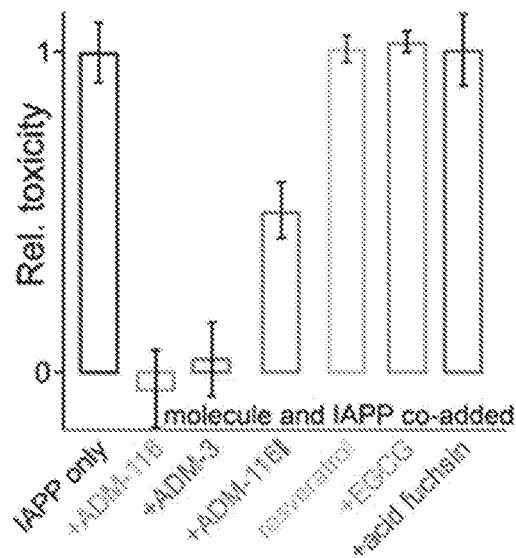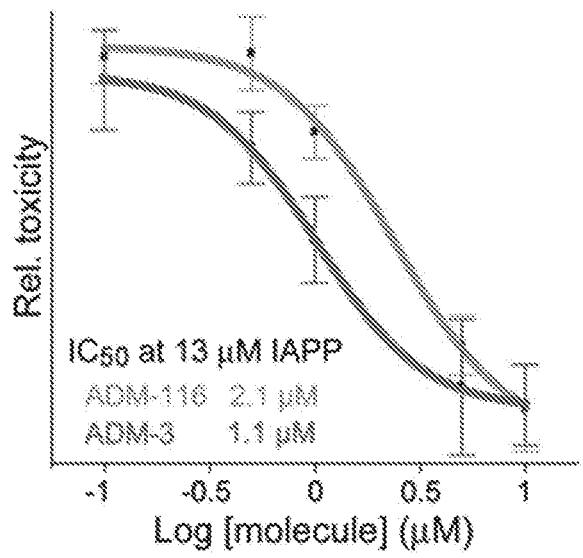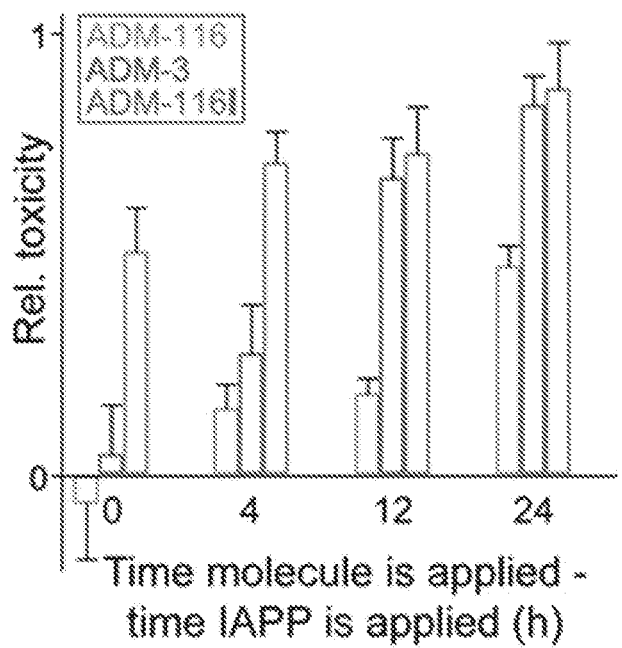

FIG. 7A
Time of IAPP addition: 0h, Time of ADM-116 addition: 20h
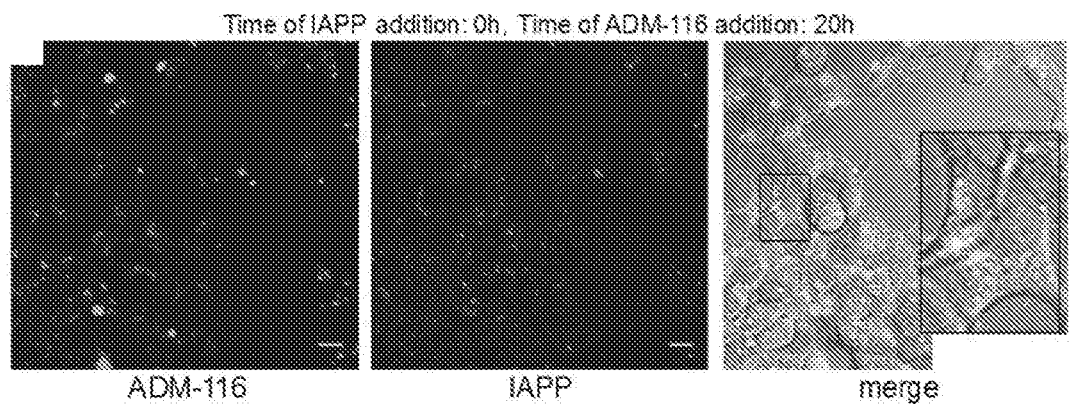
FIG. 7B
Time of IAPP addition: 0h, Time of ADM-116 addition 0h
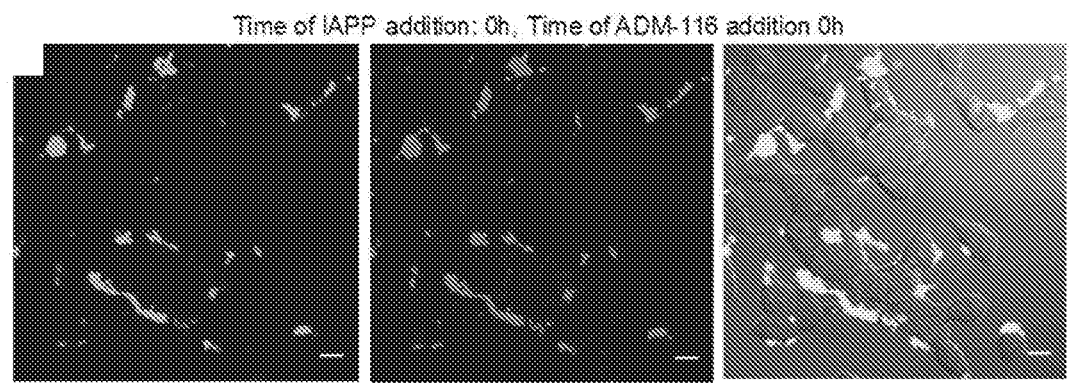
FIG. 7C
Time of IAPP addition: 0h, Time of ADM-116 addition: 18h
FIG. 7D
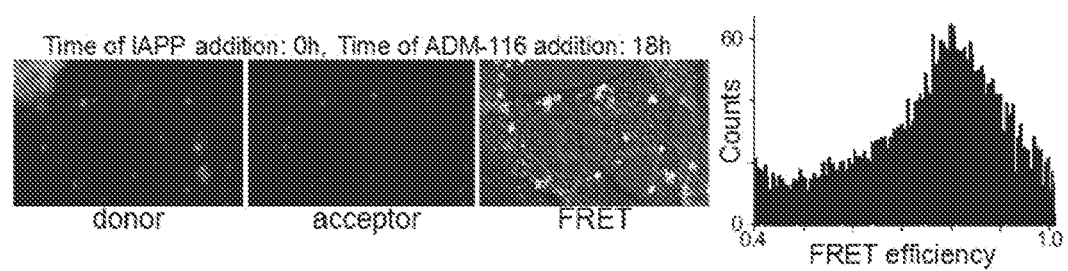

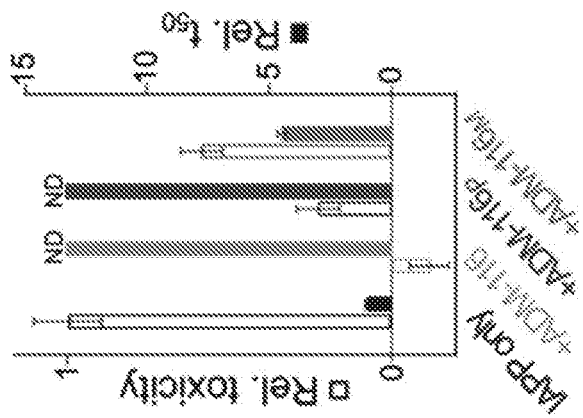
FIG. 8C
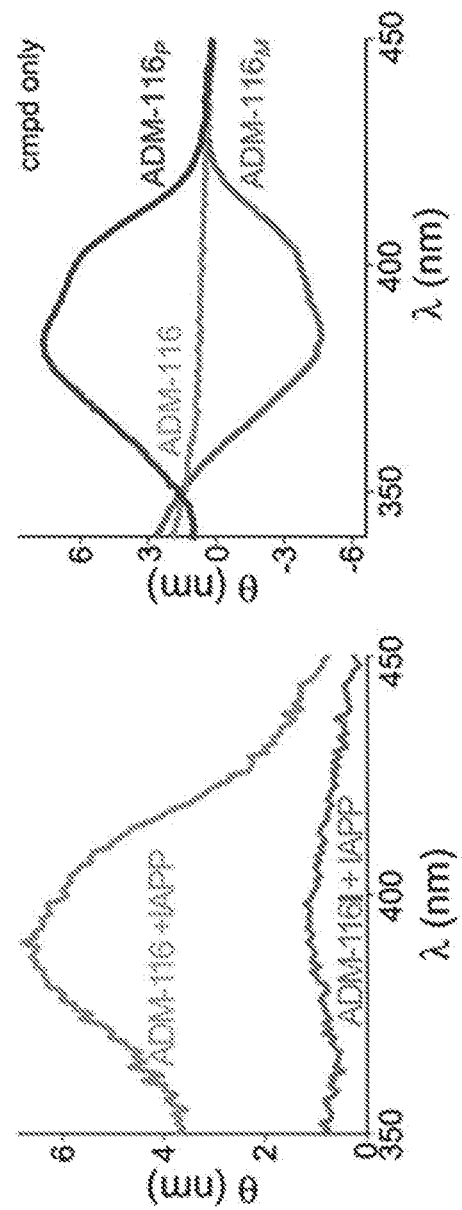
FIG. 8B
FIG. 8A

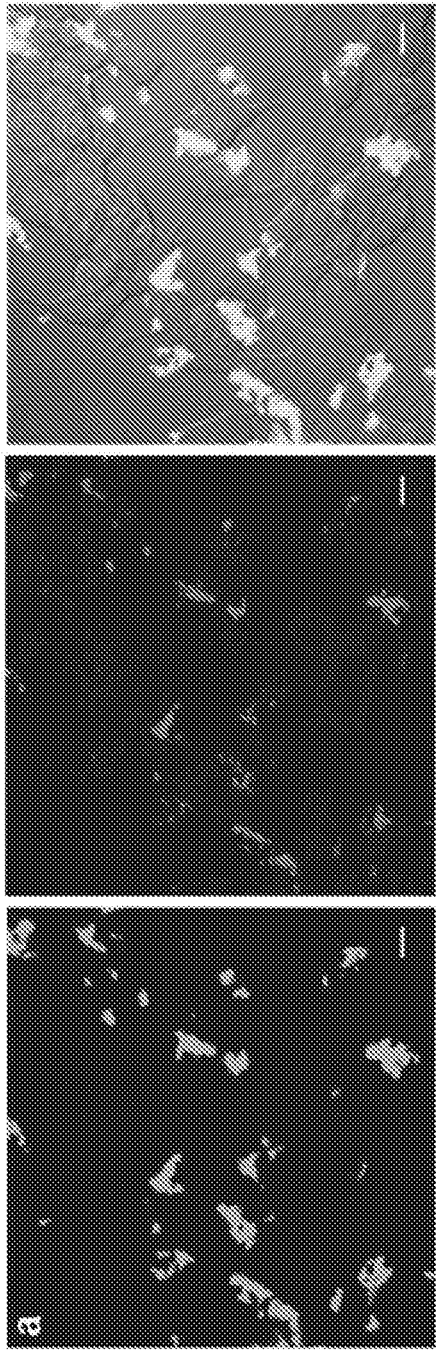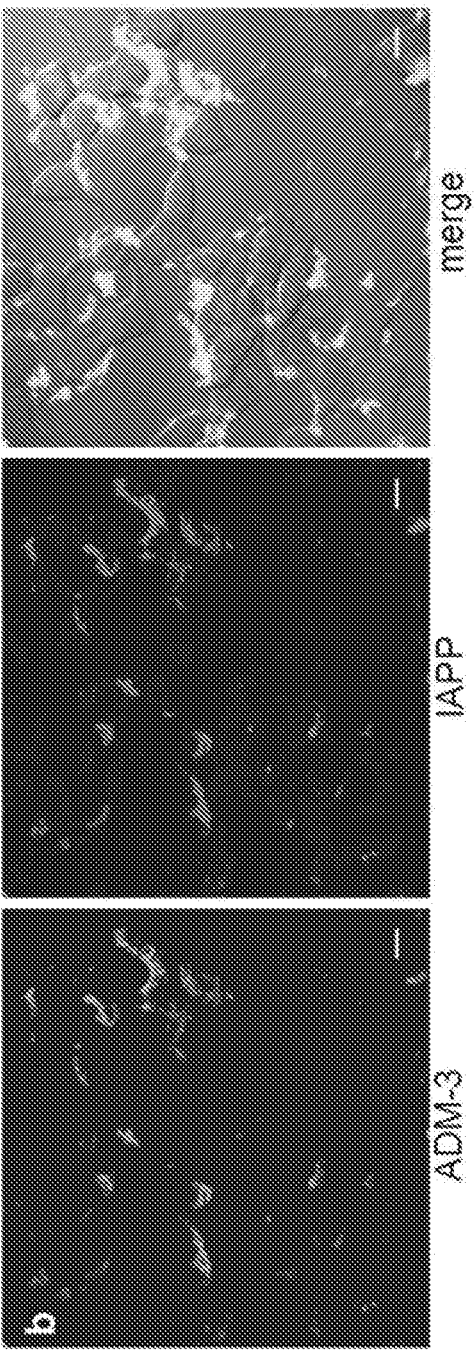

SEQUENCE LISTING

```
<160> NUMBER OF SEQ ID NOS: 1

<210> SEQ ID NO 1
<211> LENGTH: 37
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (37)..(37)
<223> OTHER INFORMATION: AMIDATION

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35
```

QUINOLINE AMIDES AND METHODS OF USING SAME

CROSS-REFERENCE TO RELATED APPLICATIONS

This present application is a 35 U.S.C. § 371 national phase application from, and claims priority to, International Application No. PCT/US2016/059007, filed Oct. 27, 2016, and published under PCT Article 21(2) in English, which claims priority under 35 U.S.C. § 119(e) to U.S. Provisional Application No. 62/247,572, filed Oct. 28, 2015, all of which are incorporated herein by reference in their entireties.

STATEMENT REGARDING FEDERALLY SPONSORED RESEARCH OR DEVELOPMENT

This invention was made with government support under GM094693 awarded by National Institutes of Health. The government has certain rights in the invention.

BACKGROUND OF THE INVENTION

Biopolymers are distinguished from artificial polymers by the presence of a specified sequence of precursors, which allows them to fold to a specific structure. A tiny set of precursors (four for DNA/RNA, and twenty for proteins) creates a breadth of folds and functions essential to life. In contrast, synthetic polymers have access to an essentially unlimited array of precursor variants; however, the lack of sequence control and unique conformation results in a breadth of function that is dwarfed by biology.

Synthetic foldamers seek to join the best of these two worlds. New scaffolds with specifiable sequences permit folded and functional structures to be successfully designed. For instance, foldamers based on oligomers of arylamides, β-peptide, α/β-peptide and peptoids have been designed to be an antimicrobial agent, agonist of GLP-1 receptor, an inhibitor of HIV-cell fusion and an antagonist of VEGF receptor 2, respectively. The achievable specificities of these small molecules rivals biopolymers.

Dynamic binding modes, such as conformational-selection, are often observed in protein-ligand interactions, such as for the anti-cancer drug Gleevec. Gleevec binds to structurally identical sites in Src and its homologue, Abl. Nevertheless, there is a >1,000-fold difference in binding affinity that can be explained by differences in protein dynamics. It stands to reason that the internal degrees of freedom of ligands should be similarly exploitable. However, ligand dynamics are viewed unfavourably as a result of entropy loss upon binding. The non-covalent and reversible stabilization of foldamer structure presents an opportunity to limit entropic loss upon protein binding without sacrificing opportunities and potential benefits of dynamic binding.

There is a need in the art for novel foldamers, which can be used to treat diseases in a mammal. The present invention addresses this unmet need.

BRIEF SUMMARY OF THE INVENTION

The invention provides a compound. The invention further provides a pharmaceutical composition comprising at least one compound of the invention and at least one pharmaceutically acceptable carrier. The invention further provides a method of preventing or treating diabetes in a subject in need thereof. The invention further provides a method of preventing or treating a neurodegenerative disease caused by a misfolded or unstructured protein. The invention further provides a method of increasing the cell membrane permeability of a molecule CARGO, wherein CARGO is selected from the group consisting of an oligonucleotide, oligodeoxynucleotide, small molecule and polypeptide. In certain embodiments, the compound is the compound of formula (I), or a salt, solvate, or N-oxide thereof, and any combinations thereof:

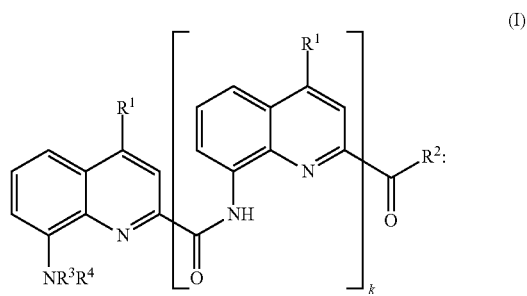

(I)

wherein each occurrence of $R^1$ is independently selected from the group consisting of —OH, —O($C_1$-$C_6$)alkyl, —O($C_1$-$C_6$)haloalkyl, —O($C_1$-$C_6$)heteroalkyl, —O($CH_2$)$_m$C(=O)O$R^5$, —OC(=O)$R^5$, —$NH_2$, —SH, —$SO_3$H and —PO(OH)$_2$; wherein $R^2$ is selected from the group consisting of —($C_1$-$C_6$)alkyl, —($C_1$-$C_6$)heteroalkyl, —O$R^5$, —($C_3$-$C_{10}$)heterocyclyl, aryl and heteroaryl, wherein the alkyl, hetereoalkyl, heterocyclyl, aryl or heteroaryl group is optionally substituted; wherein $R^3$ and $R^4$ are independently selected from the group consisting of H, —(C=O)$_{0-1}$($C_1$-$C_6$)alkyl, —(C=O)$_{0-1}$($C_3$-$C_8$)cycloalkyl, —(C=O)$_{0-1}$($C_1$-$C_6$)heteroalkyl, —(C=O)$_{0-1}$aryl, and —(C=O)$_{0-1}$heteroaryl, wherein the alkyl, cycloalkyl, aryl or heteroaryl group is optionally substituted; or $R^3$ and $R^4$, together with the nitrogen to which $R^3$ and $R^4$ are connected, form —($C_3$-$C_{10}$)heterocyclyl or —$NO_2$; wherein each occurrence of $R^5$ is independently selected from the group consisting of H, —($C_1$-$C_6$)alkyl, —($C_1$-$C_6$)heteroalkyl, —($C_3$-$C_8$)cycloalkyl, —($C_4$-$C_{10}$)heterocyclyl, aryl, and —($C_5$-$C_{10}$)heteroaryl, wherein the alkyl, heteroalkyl, cycloalkyl, heterocyclyl, aryl, or heteroaryl group is optionally substituted; wherein each occurrence of in is independently an integer ranging from 1 to 5; wherein k is an integer ranging from 1 to 5; and wherein the compound of formula (I) has a net negative charge at physiological pH. In certain embodiments, the compound is the compound of formula (II), or a salt, solvate, or N-oxide thereof, and any combinations thereof:

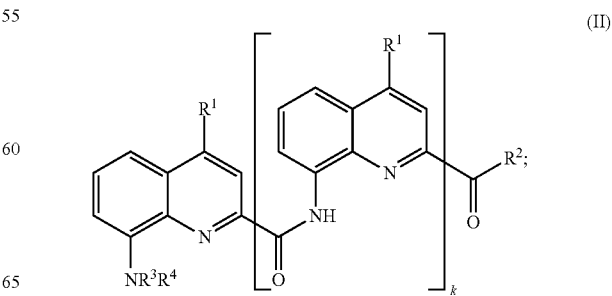

(II)

wherein each occurrence of $R^1$ is independently selected from the group consisting of —OH, —O($C_1$-$C_6$)alkyl, —O($C_1$-$C_6$)haloalkyl, —O($C_1$-$C_6$)heteroalkyl, —O($CH_2$)$_m$C(=O)O$R^5$, —OC(=O)$R^5$, —$NH_2$, —SH, —$SO_3$H and —PO(OH)$_2$; wherein (i) $R^2$ is —X1-LINKER-CARGO or (ii) $R^3$ is —X2-LINKER-CARGO; wherein X1 is a bond, —NH—, —O— or —S—; wherein X2 is —C(=O)— or —C(=S)—; wherein LINKER comprises a group consisting of —($CH_2$)$_n$—, —($CH_2CH_2O$)$_n$— and -(AA)$_n$-. wherein each occurrence of n is independently an integer ranging from 1 to 10 and wherein each occurrence of AA is independently a naturally occurring amino acid, further wherein —X-LINKER optionally further comprises a disulfide bond; and wherein CARGO is a molecule selected from an oligonucleotide, oligodeoxynucleotide, small molecule and polypeptide; wherein if $R^2$ is —X1-LINKER-CARGO, then $R^3$ and $R^4$ are independently selected from the group consisting of H, —(C=O)$_{0-1}$($C_1$-$C_6$)alkyl, —(C=O)$_{0-1}$($C_3$-$C_8$)cycloalkyl, —(C=O)$_{0-1}$($C_1$-$C_6$)heteroalkyl, —(C=O)$_{0-1}$aryl, and —(C=O)$_{0-1}$heteroaryl, wherein the alkyl, cycloalkyl, aryl or heteroaryl group is optionally substituted; or $R^3$ and $R^4$, together with the nitrogen to which $R^3$ and $R^4$ are connected, form —($C_3$-$C_{10}$)heterocyclyl or —$NO_2$; and wherein if $R^3$ is —X2-LINKER-CARGO, then $R^2$ is selected from the group consisting of —($C_1$-$C_6$)alkyl, —($C_1$-$C_6$)heteroalkyl, —O$R^5$, —($C_3$-$C_{10}$)heterocyclyl, aryl, and heteroaryl, wherein the alkyl, heteroalkyl, heterocyclyl, aryl or heteroaryl group is optionally substituted; and $R^4$ is H; wherein each occurrence of $R^5$ is independently selected from the group consisting of H, —($C_1$-$C_6$)alkyl, —($C_1$-$C_6$)heteroalkyl, —($C_3$-$C_8$)cycloalkyl, —($C_4$-$C_{10}$)heterocyclyl, aryl, and —($C_5$-$C_{10}$)heteroaryl, wherein the alkyl, heteroalkyl, cycloalkyl, heterocyclyl, aryl, or heteroaryl group is optionally substituted; wherein each occurrence of m is independently an integer ranging from 1 to 5; wherein k is an integer ranging from 1 to 5; and wherein the compound of formula (II) has a net negative charge at physiological pH.

In certain embodiments, at least one occurrence of $R^1$ is selected from the group consisting of —O($CH_2$)$_m$C(=O)OH, —$SO_3$H and —PO(OH)$_2$. In other embodiments, at least one occurrence of $R^1$ is —O($CH_2$)$_m$COOH. In yet other embodiments, at least two occurrences of $R^1$ are independently selected from the group consisting of —O($CH_2$)$_m$C(=O)OH, —$SO_3$H and —PO(OH)$_2$. In yet other embodiments, at least two occurrences of $R^1$ are independently —O($CH_2$)$_m$C(=O)OH.

In certain embodiments, every other quinoline group in (I) has a $R^1$ independently selected from the group consisting of —O($CH_2$)$_m$C(=O)OH, —$SO_3$H and —PO(OH)$_2$ at the 4-position of the respective ring.

In certain embodiments, if a given quinoline group in (I) has a $R^1$ selected from the group consisting of —O($CH_2$)$_m$C(=O)OH, —$SO_3$H and —PO(OH)$_2$ at the 4-position of the ring, the quinoline groups to which the given quinoline group is covalently linked have $R^1$ substituents that are independently selected from the group consisting of —OH, —O($C_1$-$C_6$)alkyl, —O($C_1$-$C_6$)haloalkyl, —O($C_1$-$C_6$)heteroaryl, —OC(=O)$R^5$, —$NH_2$, and —SH, at the 4-position of the corresponding rings, wherein $R^5$ is not H.

In certain embodiments, k is 3. In other embodiments, each occurrence of $R^1$ is independently selected from the group consisting of —OCH$_2$CH$_3$ and —OCH$_2$COOH; $NR^3R^4$ is —$NO_2$; $R^2$ is —OMe; and k is 3.

In certain embodiments, any two quinoline groups that are covalently linked do not have the same $R^1$ substituent.

In certain embodiments, the compound is the compound of formula (III) (IV):

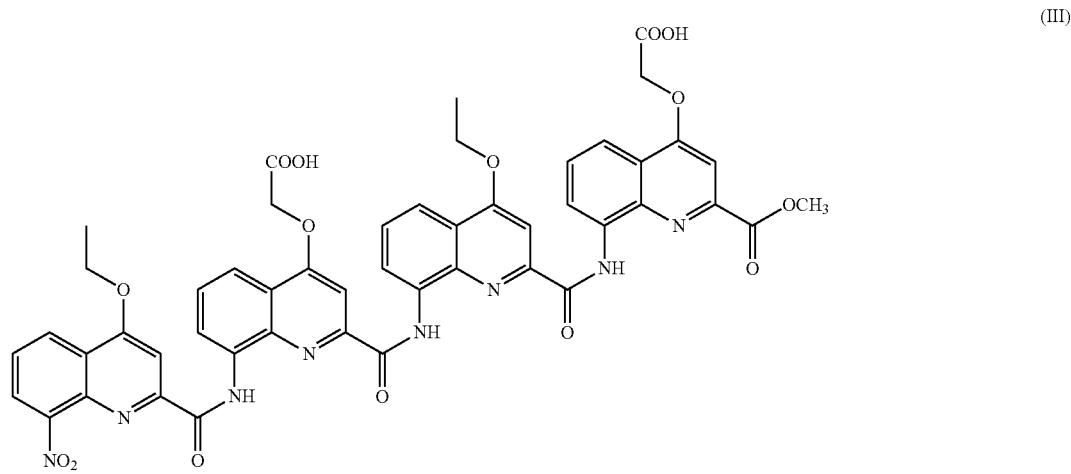

-continued

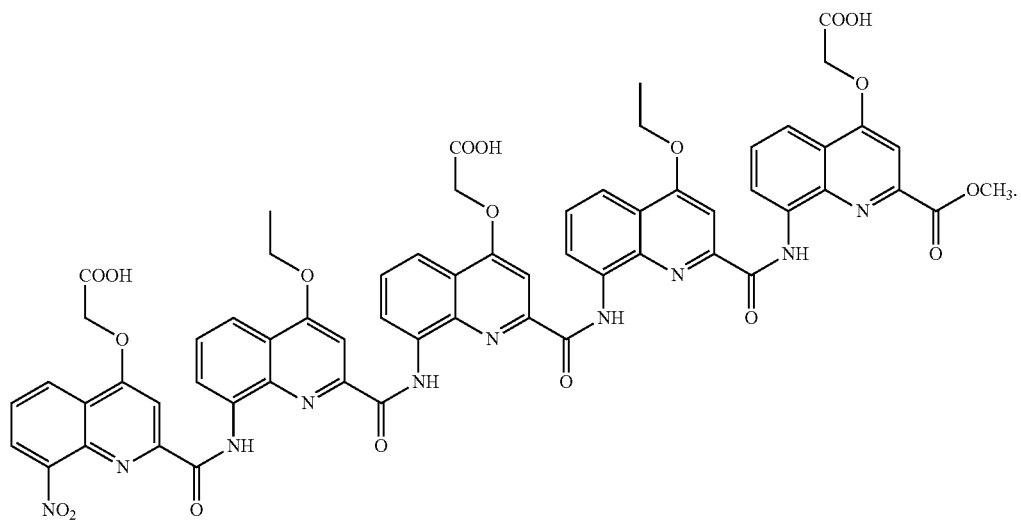

(IV)

In certain embodiments, at physiological pH the compound of formula (I) has a net negative charge that is selected from the group consisting of −1, −2, −3, −4, −5, and −6.

In certain embodiments, CARGO comprises a detectable label. in other embodiments, at physiological pH the compound of formula (II) in the absence of CARGO has a net negative charge that is selected from the group consisting of −1, −2, −3, −4, −5, and −6.

In certain embodiments, the compound is water soluble. In other embodiments, the compound is capable of passively penetrating a cell membrane.

In certain embodiments, the compound of formula (II) has higher cell membrane permeability than CARGO.

In certain embodiments, X1-LINKER or X2-LINKER is cleaved within a cell.

In certain embodiments, the compound is further coupled with a detectable label. In other embodiments, the detectable label is selected from the group consisting of a radioisotope, stable isotope, fluorophore, electron dense metals, biotin, DNA, RNA, antibody epitope, spin label, reactive peptide tag, quantum dot and any combinations thereof.

In certain embodiments, the pharmaceutical composition further comprises at least one additional therapeutic agent.

In certain embodiments, the method comprises administering to the subject a therapeutically effective amount of at least one compound of the invention. In other embodiments, the method further comprises administering to the subject at least one additional therapeutic agent that treats or prevents diabetes. In yet other embodiments, the method further comprises administering to the subject at least one additional therapeutic agent that treats or prevents the neurodegenerative disease.

In certain embodiments, the compound and the at least one additional therapeutic agent are co-administered to the subject. In other embodiments, the compound and the at least one additional therapeutic agent are co-formulated.

In certain embodiments, the diabetes is type I or type II diabetes. In other embodiments, the protein comprises α-synuclein, tau or Aβ. In yet other embodiments, the neurodegenerative disease comprises Parkinson's or Alzheimer's Disease. In yet other embodiments, the subject is a human.

In certain embodiments, the method comprises derivatizing CARGO to form a compound of formula (II). In other embodiments, the compound is cleaved within the cell releasing CARGO or a derivative thereof, wherein the derivative of CARGO has essentially the same biological activity as CARGO.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 3A illustrates 10 μM IAPP fibre formation over time catalysed by unilamellar vesicles (630 μM monomer units, dioleoylphosphatidylglycerol (DOPB): dioleoylphosphatidylcholine (DOPC)=1:1, 100 nm). FIG. 3B illustrates inhibition with the indicated small molecules performed at IAPP:small molecule=1:1 (reaction midpoints, $t_{50}$). Inset illustrates statistics of dose dependence of inhibition of fibre formation by ADM 116.

FIGS. 4A-4C illustrate rescue of INS-1 cells from IAPP induced toxicity. FIG. 4A illustrates statistics of toxic effect of 13 μM IAPP applied at time-zero to INS-1 cells and measured 48 h later using Cell-Titer Blue (CTB). Data are shown for IAPP alone and with equimolar ratio of the indicated small molecule co-added at 1:1 ratio. Data are renormalized to the toxicity induced only by IAPP. FIG. 4B illustrates dose dependence of toxic rescue by ADM-3 and ADM-116. FIG. 4C illustrates relative toxicity of 13 μM IAPP in which a time delay is introduced between addition of IAPP and addition of molecule. Error bars in FIGS. 4A-4C are standard deviations from three sets of experiments conducted on separate occasions.

FIG. 5A illustrates relative binding of ADM-116 to IAPP using 25 nM ADM-116$_F$, obtained by measuring diffusion by fluorescence correlation spectroscopy (FCS) as a function of IAPP. Inset illustrates representative raw autocorrelation data (black) and two component fit (red) for 0 nM and 250 nM IAPP respectively. FIG. 5B illustrates association constants for the indicated small molecule with human IAPP measured by Isothermal titration calorimetry (ITC). ND=undetectable binding. Inset illustrates representative raw data and fit for ADM-116 binding plotted as a function of stoichiometry. FIG. 5C illustrates free energy and entropy contributions to binding by ITC for the indicated compounds. FIG. 5D illustrates far UV CD spectra of 25 μM IAPP in the presence of large unilamellar vesicles (LUVs) (1.2 mM in monomeric units, DOPG:DOPC=1:1, 100 nm). Shown are two time points for IAPP alone (blue, black) and with addition of stoichiometric ADM-116 at t=0. ADM-116 without IAPP is shown as control (orange).

FIG. 6A depicts confocal fluorescence images of INS 1 cells incubated for 12 h with 200 nM ADM-116$_F$ or 200 nM ADM-3$_F$. Conditions shown are with and without addition of a further 15 μM of unlabelled small molecule. FIG. 6B depicts confocal fluorescence images giant plasma membrane derived vesicles (GPMVs) prepared from INS-1 cells incubated for 24 h with 200 nM ADM-116$_F$ or ADM-3$_F$ mixed with 10 μM of unlabelled compound. FIG. 6C illustrates calculated versus measured octanol:water partition coefficients for time three molecules: ADM-116. ADM-116I, and ADM-3.

FIGS. 7A-7D illustrate colocalization of IAPP and ADM-116. FIG. 7A comprises a series of images illustrating INS-1 cells exposed to a rescued condition doped with fluorescent variants of protein and ligand (13 μM IAPP, 15 μM ADM-116, 100 nM IAPP$_{A594}$ and 200 nM ADM-116$_F$). The small molecule and IAPP were co-introduced to the culture media. FIG. 7B comprises a series of images illustrating INS-1 cells exposed to a rescued condition doped with fluorescent variants of protein and ligand (13 μM IAPP, 15 μM ADM-116, 100 nM IAPP$_{A594}$ and 200 nM ADM-116$_F$). The small molecule was added 20 hours after IAPP introduced to the culture media. FIG. 7C comprises a series of images illustrating INS-1 cells exposed to a rescued condition doped with fluorescent variants of protein and ligand (13 μM IAPP, 15 μM ADM-116, 100 nM IAPP$_{A594}$ and 200 nM ADM-116$_F$). The rescued condition was the same as that depicted in FIG. 7B, but without the unlabelled components and initial incubation with IAPP preformed for 18 h. Confocal fluorescence images were collected at the acceptor's emission wavelength using donor (left) or acceptor excitation light (middle). FRET was computed from these channels and are shown as white dots on a DIC image of a representative cell. Only areas showing a FRET efficiency of >0.4 are shown as values below this are indistinguishable from background. Background FRET was determined using parallel experiments which included a further 13 μM of unlabelled IAPP (FIG. 14). FIG. 7D is a FRET histogram depicting the total counts at the indicated FRET efficiencies across ~50 regions of interest.

FIGS. 8A-8C illustrate selection, perturbation and activity of ADM-116 analogs. FIG. 8A depicts visible CD of 25 μM ADM-116 or ADM-116I in the presence of 25 μM IAPP. FIG. 8B depicts visible CD of ADM-116 and each of two chiral variants designed to introduce bias into the ADM-116 enantiomer distribution. FIG. 8C depicts comparison of the fibre formation inhibition and toxic rescue activities of enantiomer biased constructs of ADM-116. Experiment conditions match those used in FIGS. 3A-3B and FIGS. 4A-4C respectively.

FIG. 9A illustrates three representative kinetic profiles for a standard reaction of 10 μM IAPP catalysed by the presence of 630 μM LUVs (DOPG:DOPC=1:1, 100 nm). Inset illustrates a representative sigmoid fit (magenta) used to extract reaction midpoints, $t_{50}$. FIG. 9B illustrates representative comparison of the kinetic profiles of (10 μM) IAPP fibrillation in the absence (black) and presence (red) of 630 μM LUVs. All experiments were conducted at least in triplicate with errors reported as ±one standard deviation.

FIG. 10A depicts negative stain transmission electron microscopy (TEM) images of liposome catalysed IAPP (10 μM) self-assembly in the absence of 10 μM ADM-116. FIG. 10B depicts negative stain TEM images of liposome catalysed IAPP (10 μM) self-assembly in the presence of 10 μM ADM-116.

FIGS. 13A-13B illustrate colocalization of IAPP and ADM-3. INS-1 cells were exposed to a rescued condition (13 μM IAPP and 15 μM ADM-3) doped with 200 nM ADM-3$_F$ and 100 nM IAPP$_{A594}$) FIG. 13A comprises a series of images of INS-1 cells when IAPP and small molecule were added at the same time to culture media. FIG. 13B comprises a series of images of INS-1 cells when ADM-3 was added 20 h after addition of IAPP.

FIG. 16A illustrates visible CD spectra of 25 μM ADM-116 or ADM-116$_P$ in the presence of liposome (630 μM in monomer units, DOPG:DOPC=1:1. 100 nm) and 25 μM IAPP. FIG. 16B illustrates far-UV CD spectra of 25 μM IAPP in the presence of ADM-116 or ADM-116I at a ratio of 1:0.5 (IAPP:small molecule).

DETAILED DESCRIPTION OF THE INVENTION

Figure 1A:
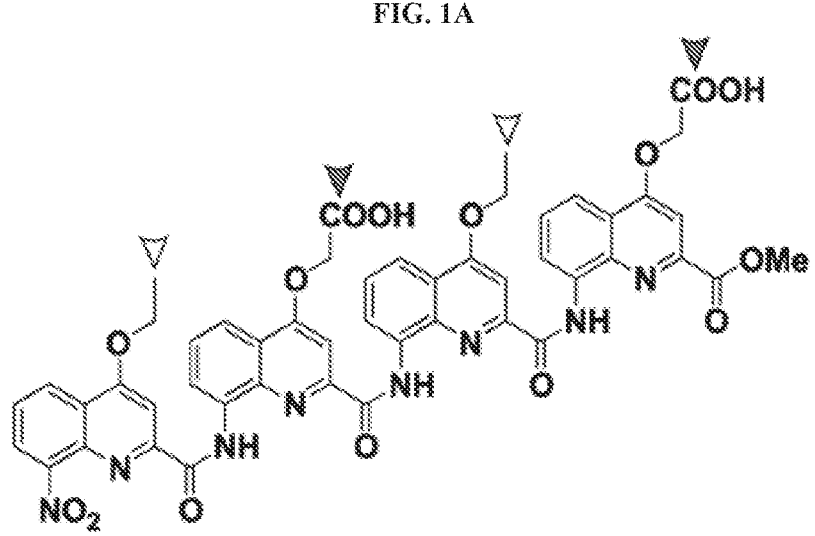
FIG. 1A depicts chemical structure of ADM 116, also denoted as compound of formula (III). Arrows indicate surface exposed functional moieties.

The present invention relates in part to the unexpected discovery of novel quinoline foldamers that bind to islet amyloid polypeptide (IAPP) and prevent the formation of (toxic) amyloid states of IAPP in a mammal. In certain embodiments, the compounds of the invention can be used to treat or prevent Type I and/or Type II diabetes in a mammal, such as a human. In other embodiments, the compounds of the invention can be used to treat neurodegenerative diseases based on misfolded and/or unstructured proteins. Exemplary proteins contemplated within the invention include α-synuclein (Parkinson's Disease), tau (Alzheimer's Disease) and/or Aβ (Alzheimer's Disease).

The present invention further provides quinoline foldamer conjugates of various biologically active compounds, wherein the conjugates have improved cell membrane permeability over the corresponding compounds.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g. age, treatment, time of day, etc.) from those organisms, tissues, cells or components thereof that display the "normal" (expected) respective characteristic. Characteristics that are normal or expected for one cell or tissue type might be abnormal for a different cell or tissue type.

As used herein, the term "ADM-118" refers to the following compound, or a salt, solvate or N-oxide thereof:

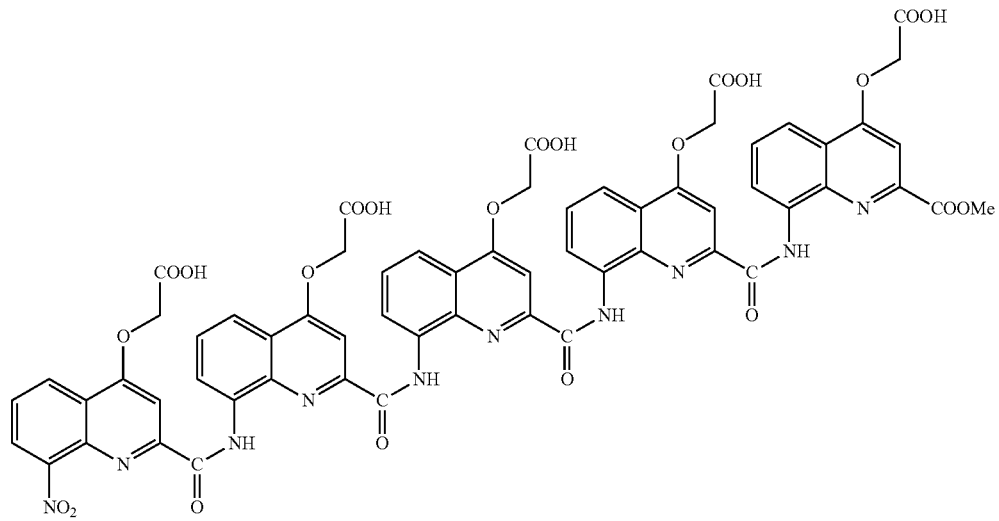 [SMILES: COC(=O)c1cc(OCC(=O)O)c2cccc(NC(=O)c3cc(OCC(=O)O)c4cccc(NC(=O)c5cc(OCC(=O)O)c6cccc(NC(=O)c7cc(OCC(=O)O)c8cccc(NC(=O)c9cc(OCC(=O)O)c%10cccc([N+](=O)[O-])c%10n9)c8n7)c6n5)c4n3)c2n1]

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art: including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co.; 1985, Easton, Pa.), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

As used herein, the term "small molecule" refers to a molecule of <2,000 amu.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

A "therapeutic" treatment is a treatment administered to a subject who exhibits signs of pathology, for the purpose of diminishing or eliminating those signs.

As used herein, the wan "alkyl," by itself or as part of another substituent means, unless otherwise stated, a straight or branched chain hydrocarbon having the number of carbon atoms designated $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "haloalkyl" means alkyl as defined above, substituted by one, two or three substituents selected from the group consisting of F, Cl, Br, and I.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized or substituted. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_3$—S—CH$_2$—CH$_3$, —NH—(CH$_2$)$_m$—OH (m=1-6), —N(CH$_3$)—(CH$_2$)$_m$—OH (m=1-6), —NH—(CH$_2$)$_m$—OCH$_3$ (m=1-6), and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy. ethoxy, 1-propoxy, 2-propoxy (isopropoxy) and the higher homologs and isomers. Preferred are (C$_1$-C$_3$) alkoxy, particularly ethoxy arid methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limited to, the following moieties:

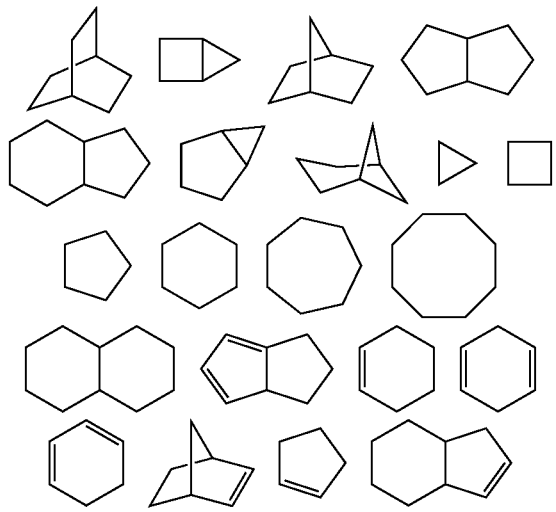

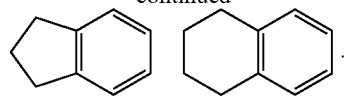

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

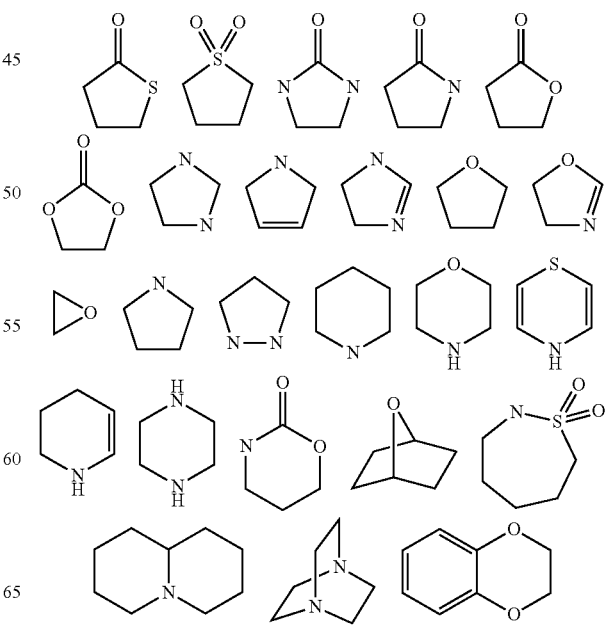

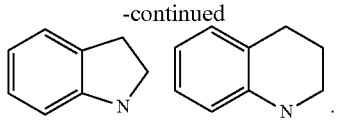
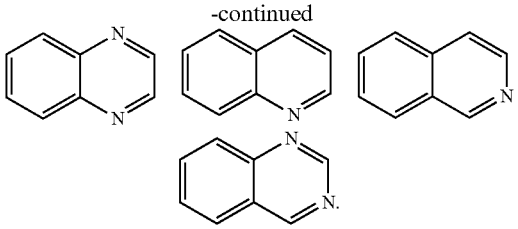

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —CH$_2$CH$_2$-phenyl. Preferred is aryl-CH$_2$— and aryl-CH(CH$_3$)—. The term "substituted aryl-($C_1$-$C_3$)alkyl" means an aryl-($C_1$-$C_3$)alkyl functional group in which the aryl group is substituted. Preferred is substituted aryl(CH$_2$)—. Similarly, the term "heteroaryl-($C_1$-$C_3$)alkyl" means a functional group wherein a one to three carbon alkylene chain is attached to a heteroaryl group, e.g., —CH$_2$CH$_2$-pyridyl. Preferred is heteroaryl-(CH$_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-(CH$_2$)—.

As used herein, the term "heteroaryl" or "heteroaromatic" refers to a heterocycle having aromatic character. A polycyclic heteroaryl may include one or more rings that are partially saturated. Examples include the following moieties:

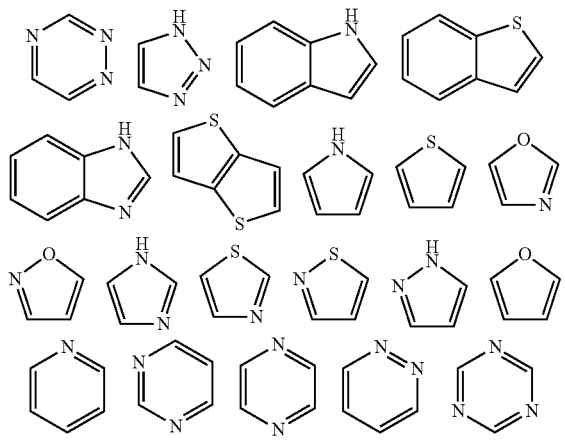

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-. 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. in other embodiments, the referenced group is optionally substituted with one or more additional group(s) individually and independently selected from groups described herein.

In certain embodiments, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]₂, and —C(NH₂)[substituted or unsubstituted alkyl]₂. In other embodiments, by way of example, an optional substituent is selected from oxo, fluorine, chlorine, bromine, iodine, —CN, —NH₂, —OH, —NH(CH₃), —N(CH₃)₂, —CH₃, —CH₂CH₃, —CH(CH₃)₂, —CF₃, —CH₂CF₃, —OCH₃, —OCH₂CH₃, —OCH(CH₃)₂, —OCF₃, —OCH₂CF₃, —S(=O)₂—CH₃, —C(=O)NH₂,—C(=O)—NHCH₃, —NHC(=O)NHCH₃, —C(=O)CH₃, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet other embodiments, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates in part to unexpected discovery of novel compounds, such as quinolone foldamers, that bind to islet amyloid polypeptide (IAPP) and prevent the formation of (toxic) amyloid states of IAPP in a mammal. The present invention also relates to a method for treating or preventing diabetes by administering to a mammal in need thereof a therapeutically effective amount of a quinoline foldamer of the invention. The present invention also relates to a method for treating or preventing neurodegenerative diseases based on misfolded and/or unstructured proteins, such as α-synuclein (Parkinson's), tau (Alzheimer's) and/or Aβ (Alzheimer's).

Figure 1B:
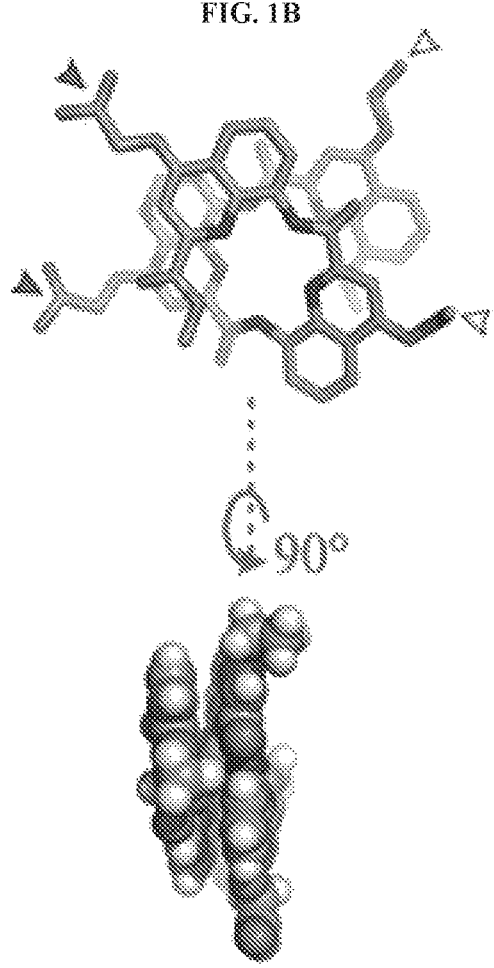
FIG. 1B depicts three-dimensional stick (top) and sphere (bottom) model of ADM 116. Arrows indicate surface exposed functional moieties.
Figures 1C, 1D:
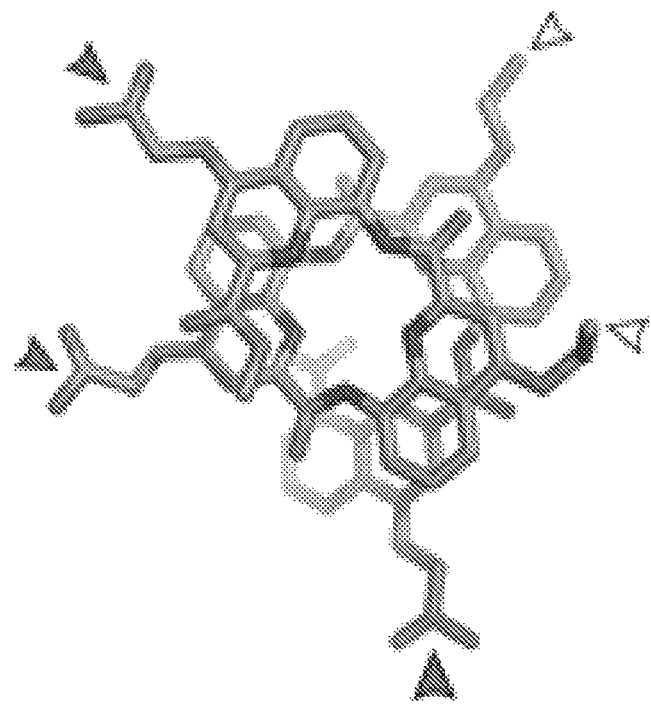
FIG. 1C illustrates the primary sequence of human islet amyloid polypeptide (IAPP; SEQ ID NO:1), which is C-terminally amidated.
FIG. 1D depicts three-dimensional stick model of pentaquinoline, ADM-116I. Arrows indicate surface exposed functional moieties.

Disordered proteins, such as those central to Alzheimer's and Parkinson's, are particularly intractable for structure-targeted therapeutic design. The present results demonstrate the capacity of a synthetic foldamer to capture structure in a disease relevant peptide. Oligoquinoline amides have a defined fold with a solvent-excluded core that is independent of its outwardly projected, derivitizable moieties. IAPP is a 37-residue peptide co-packaged with insulin in pancreatic β-cells (FIG. 1C). Aggregation of this peptide into amyloid fibres is observed in type II diabetes, and pre-amyloid states of IAPP are toxins resulting in β-cell death. The compounds of the invention comprise tetraquinolines that stabilize a pre-amyloid, α-helical conformation of IAPP. The charged, polyanionic compounds of the invention are highly soluble, yet cross biological membranes without cellular assistance. Without wishing to be limited by any theory, this may take place because the compounds are able to reversibly fold into a membrane-permeable structure. The compounds of the invention antagonize toxicity long after cellular uptake of IAPP is complete. These gains-of-function are dependent on the capacity of the foldamer to not only recognize IAPP, but also to transiently sample unfolded states. The compounds of the invention dock specifically with intracellular IAPP and rescues β-cells from apoptosis. Without wishing to be limited by any theory, the present results indicate that stabilizing non-toxic conformers of a plastic protein can be a viable strategy for cytotoxic rescue.

Without wishing to be limited by any theory, the modes of action of IAPP are similar to those of polypeptides involved in degenerative diseases, including AP peptide from Alzheimer's Disease and α-synuclein from Parkinson's disease. In all of these diseases, polypeptides are predominantly disordered in aqueous solution, and undergo disorder to α-helical transitions upon interaction with biological membranes. These interactions are associated with cell toxicity relevant to disease. In certain embodiments, the compounds of the invention are useful in treating and/or preventing degenerative diseases including Alzheimer's Disease and Parkinson's disease Compounds The compounds of the present invention may be synthesized using techniques well-known in the art of organic synthesis. The starting materials and intermediates required for the synthesis may be obtained from commercial sources or synthesized according to methods known to those skilled in the art.

In one aspect, the invention provides a compound of formula (I), a salt, solvate, or N-oxide thereof:

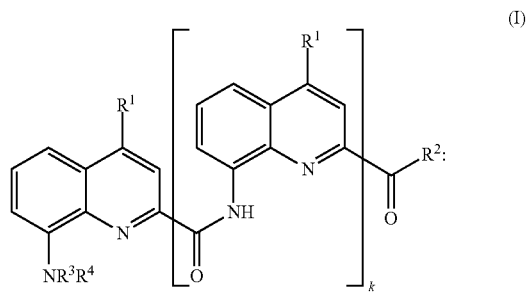

wherein each occurrence of R¹ is independently selected from the group consisting of —OH, —O(C₁-C₆)alkyl, —O(C₁-C₆)haloalkyl, —O(C₁-C₆)heteroalkyl, —O(CH₂)$_m$C(=O)OR⁵, —OC(=O)R⁵, —NH₂, —SH, —SO₃H and —PO(OH)₂;

wherein R² is selected from the group consisting of —(C₁-C₆)alkyl, —(C₁-C₆)heteroalkyl, —OR⁵, —(C₃-C₁₀)heterocyclyl, aryl and heteroaryl, wherein the alkyl, hetereoalkyl, heterocyclyl, aryl or heteroaryl group is optionally substituted;

wherein R³ and R⁴ are independently selected from the group consisting of H, —(C=O)$_{0-1}$(C₁-C₆)alkyl, —(C=O)$_{0-1}$(C₃-C₈)cycloalkyl, —(C=O)$_{0-1}$(C₁-C₆)heteroalkyl, —(C=O)$_{0-1}$aryl, and —(C=O)$_{0-1}$heteroaryl, wherein the alkyl, cycloalkyl, aryl or heteroaryl group is optionally substituted; or R³ and R⁴, together with the nitrogen to which R³ and R⁴ are connected, form —(C₃-C₁₀)heterocyclyl or —NO₂;

wherein each occurrence of R⁵ is independently selected from the group consisting of H, —(C₁-C₆)alkyl, —(C₁-C₆)heteroalkyl, —(C₁-C₈)cycloalkyl, —(C₄-C₁₀)heterocyclyl, aryl, and —(C₅-C₁₀)heteroaryl, wherein the alkyl, heteroalkyl, cycloalkyl, heterocyclyl, aryl, or heteroaryl group is optionally substituted;

wherein each occurrence of m is independently an integer ranging from 1 to 5;
wherein k is an integer ranging from 1 to 5;
wherein the compound of formula (I) has a net negative charge at physiological pH.

In another aspect, the invention provides a compound of formula (II), a salt, solvate, or N-oxide thereof:

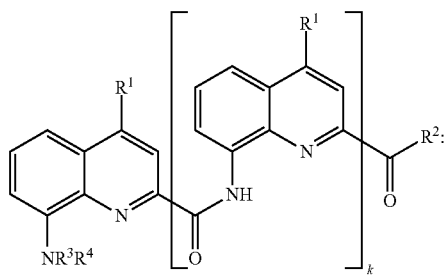

wherein each occurrence of $R^1$ is independently selected from the group consisting of —OH, —O($C_1$-$C_6$)alkyl, —O($C_1$-$C_6$)haloalkyl, —O($C_1$-$C_6$)heteroalkyl, —O($CH_2$)$_m$C(=O)O$R^5$, —OC(=O)$R^5$, —$NH_2$, —SH, —$SO_3$H and —PO(OH)$_2$;
wherein (i) $R^2$ is —X1-LINKER-CARGO or (ii) $R^3$ is —X2-LINKER-CARGO;
X1 is a bond, —NH—, —O— or —S—;
X2 is —C(=O)— or —C(=S)—;
LINKER comprises a group consisting of —($CH_2$)$_n$—, —($CH_2CH_2O$)$_n$— and -(AA)$_n$-, wherein each occurrence of n is independently an integer ranging from 1 to 10 and wherein each occurrence of AA is independently an amino acid, further wherein —X-LINKER optionally further comprises a disulfide bond; and
CARGO is a molecule selected from an oligonucleotide, oligodeoxynucleotide, small molecule and polypeptide;
wherein if $R^2$ is —X1-LINKER-CARGO, then $R^3$ and $R^4$ are independently selected from the group consisting of H, —(C=O)$_{0-1}$($C_1$-$C_6$)alkyl, —(C=O)$_{0-1}$($C_1$-$C_8$)cycloalkyl, —(C=O)$_{0-1}$($C_1$-$C_6$)heteroalkyl, —(C=O)$_{0-1}$aryl, and —(C=O)$_{0-1}$heteroaryl, wherein the alkyl, cycloalkyl, aryl or heteroaryl group is optionally substituted; or $R^3$ and $R^4$, together with the nitrogen to which $R^3$ and $R^4$ are connected, form —($C_3$-$C_{10}$)heterocyclyl or —$NO_2$; and
wherein if $R^3$ is —X2-LINKER-CARGO, then $R^2$ is selected from the group consisting of —($C_1$-$C_6$)alkyl, —($C_1$-$C_6$)heteroalkyl, —($C_1$-$C_{10}$)heterocyclyl, aryl, and heteroaryl, wherein the alkyl, heteroalkyl, heterocyclyl, aryl or heteroaryl group is optionally substituted.; and $R^4$ is H;
wherein each occurrence of $R^5$ is independently selected from the group consisting of H, —($C_1$-$C_6$)alkyl, —($C_1$-$C_6$)heteroalkyl, —($C_3$-$C_8$)cycloalkyl, —($C_4$-$C_{10}$)heterocyclyl, aryl, and —($C_5$-$C_{10}$)heteroaryl, wherein the alkyl, heteroalkyl, cycloalkyl, heterocyclyl, aryl, or heteroaryl group is optionally substituted;
wherein each occurrence of m is independently an integer ranging from 1 to 5;
wherein k is an integer ranging from 1 to 5; and
wherein the compound of formula (II) in the absence of CARGO has a net negative charge at physiological pH.

In certain embodiments, the compound of formula (I) has a net negative charge of −1 at physiological pH. In other embodiments, the compound of formula (I) has a net negative charge of −2 at physiological pH. In yet other embodiments, the compound of formula (I) has a net negative charge of −3 at physiological pH. In yet other embodiments, the compound of formula (I) has a net negative charge of −4 at physiological pH. In yet other embodiments, the compound of formula (I) has a net negative charge of −5 at physiological pH. In yet other embodiments, the compound of formula (I) has a net negative charge of −6 at physiological pH.

In certain embodiments, the compound of formula (II) in the absence of CARGO has a net negative charge of −1 at physiological pH. In other embodiments, the compound of formula (II) in the absence of CARGO has a net negative charge of −2 at physiological pH. In yet other embodiments, the compound of formula (II) in the absence of CARGO has a net negative charge of −3 at physiological pH. In yet other embodiments, the compound of formula (II) in the absence of CARGO has a net negative charge of −4 at physiological pH. In yet other embodiments, the compound of formula (II) in the absence of CARGO has a net negative charge of −5 at physiological pH. In yet other embodiments, the compound of formula (II) in the absence of CARGO has a net negative charge of −6 at physiological pH.

In certain embodiments, CARGO comprises a detectable label. In other embodiments, the detectable label is selected from the group consisting of a radioisotope, stable isotope, fluorophore, electron dense metals, biotin, DNA, RNA, antibody epitope, spin label, reactive peptide tag (such as FLASH tag), quantum dot, and any combinations thereof.

In certain embodiments, at least one occurrence of $R^1$ is selected from the group consisting of —O($CH_2$)$_m$C(=O)OH, —$SO_3$H and —PO(OH)$_2$. In other embodiments, at least two occurrences of $R^1$ are independently selected from the group consisting of —O($CH_2$)$_m$C(=O)OH, —$SO_3$H and —PO(OH)$_2$.

In certain embodiments, at least one occurrence of $R^1$ is —O($CH_2$)$_m$COOH. In other embodiments, at least two occurrences of $R^1$ are independently —O($CH_2$)$_m$COOH.

In certain embodiments, every other quinoline group in (I) has a $R^1$ selected from the group consisting of —O($CH_2$)$_m$C(=O)OH, —$SO_3$H and —PO(OH)$_2$ at the 4-position of the respective ring. In other embodiments, if a given quinoline group in (I) has a $R^1$ selected from the group consisting of —O($CH_2$)$_m$C(=O)OH, —$SO_3$H and —PO(OH)$_2$ at the 4-position of the ring, the quinoline groups to which the given quinoline group is covalently linked have $R^1$ substituents that are independently selected from the group consisting of —OH, —O($C_1$-$C_6$)alkyl, —O($C_1$-$C_6$)haloalkyl, —O($C_1$-$C_6$)heteroalkyl, —OC(=O)$R^5$, —$NH_2$, and —SH, at the 4-position of the corresponding rings, wherein $R^5$ is not H.

In certain embodiments, k is 1. In other embodiments, k is 2. In yet other embodiments, k is 3. In yet other embodiments, k is 4. In yet other embodiments, k is 5.

In certain embodiments, each occurrence of $R^1$ is independently selected from the group consisting of —OCH$_2$CH$_3$ and —OCH$_2$COOH; $NR^3R^4$ is —$NO_2$; $R^2$ is —OMe; and k=3.

In certain embodiments each occurrence of $R^1$ is independently selected from the group consisting of —OCH$_2$CH$_3$ and —OCH$_2$COOH, wherein any two quinoline groups that are covalently linked do not have the same $R^1$ substituent (such as, but not limited to, compounds (III) and (IV)).

In yet other embodiments, —$NR^3R^4$ is —$NO_2$ and $R^2$ is —OMe.

Exemplary compounds of the invention include formulas (III)-(IV). The compound of formula (III) is also denoted as ADM-116. The compound of formula (IV) is also denoted as ADM-116I.

compounds described herein comprise a covalently linked chiral auxiliary (such as but not limited to a camphenyl group). In yet other embodiments, compounds described herein interact with a target molecule, and this interaction

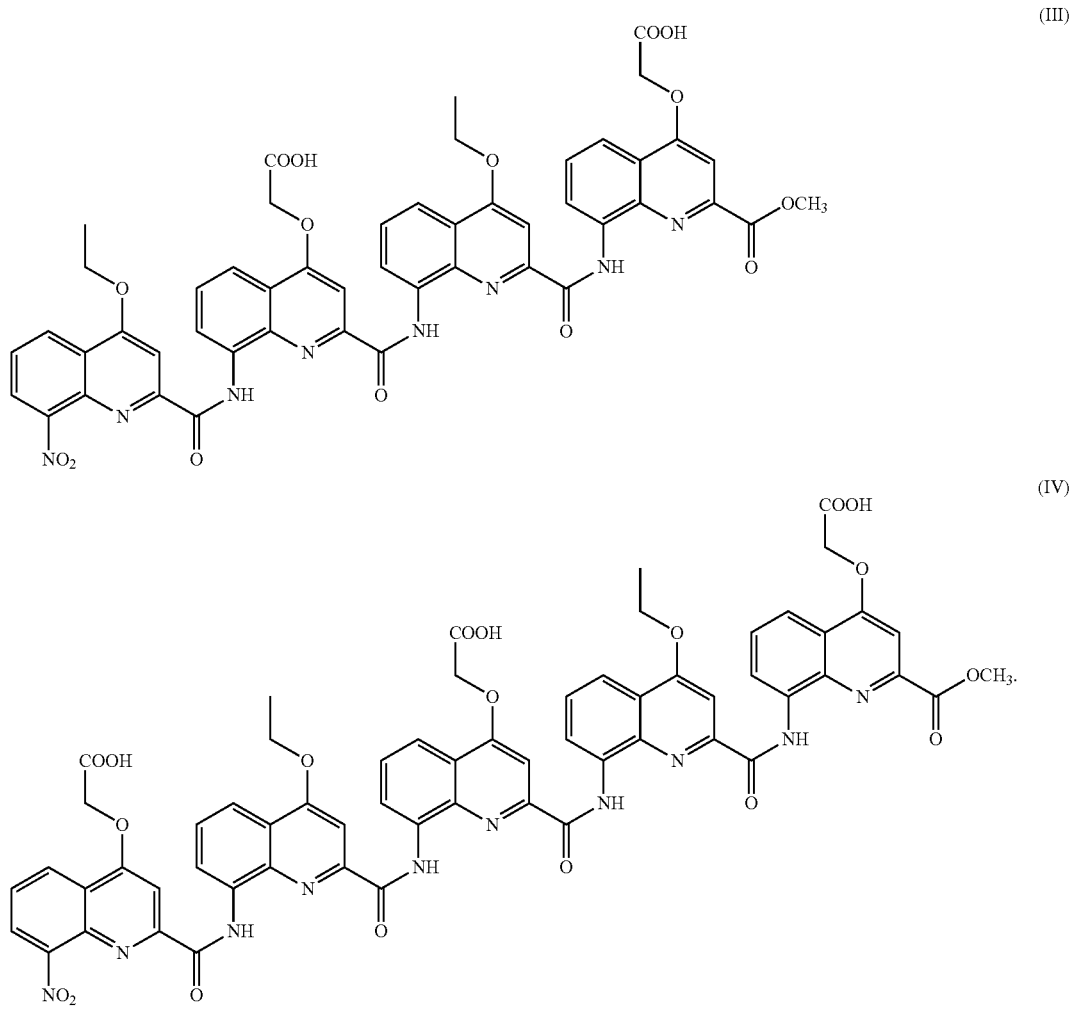

In certain embodiments, the compounds of the invention are water soluble. In other embodiment, the compounds of the invention are capable of passively penetrating a cell membrane. In yet other embodiments, the compounds of the invention reversibly folds into a cell-permeable structure which has a hydrophobic core.

In certain embodiments, the compound of formula (II) has higher cell membrane permeability than CARGO itself In other embodiments, the compound of formula (II) is cleaved within the cell to release CARGO and/or a derivative of CARGO, which has essentially the same biological activity as CARGO itself.

Synthesis

The compounds of the invention may be prepared by the general schemes described herein, using the synthetic method known by those skilled in the art.

The compounds of the invention may possess one or more stereocenters, and each stereocenter may exist independently in either the (R) or (S) configuration. In certain embodiments, compounds described herein are present in optically active or racemic forms. In other embodiments, inducing the folding of the compounds into a target driven biased folded state. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline foams (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}$H, $^{3}$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced. Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

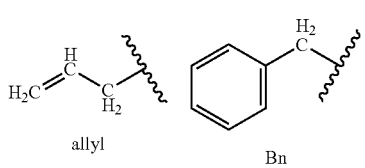

allyl        Bn

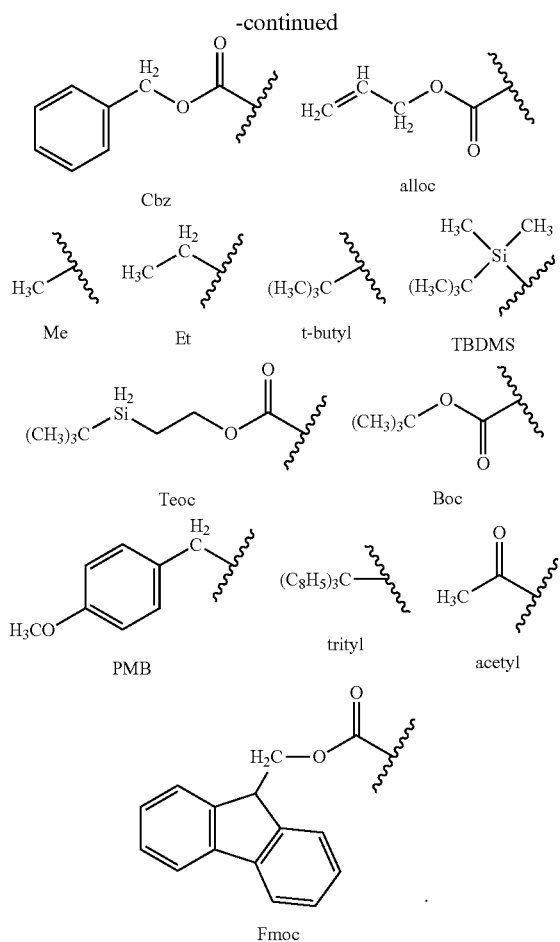

Other protecting groups, plus a detailed description of techniques applicable to the creation of protecting groups and their removal are described in Greene Wuts, Protective Groups in Organic Synthesis, 3rd Ed., John Wiley & Sons, New York, NY, 1999. and Kocienski, Protective Groups, Thieme Verlag, New York, N.Y., 1994, which are incorporated herein by reference for such disclosure.

Compositions

The invention includes a pharmaceutical composition comprising at least one compound of the invention. In certain embodiments, the composition further comprises at least one additional therapeutic agent that treats or prevents diabetes.

In certain embodiments, the compound or pharmaceutical composition and the at least one additional therapeutic agent are co-administered to the subject. In other embodiments, the compound or pharmaceutical composition and the at least one additional therapeutic agent are co-formulated.

Methods

The invention includes a method of treating or preventing diabetes in a subject in need thereof. The invention further includes a method of treating or preventing a neurodegenerative disease based on misfolded and/or unstructured proteins, such Parkinson's and/or Alzheimer's Disease.

The method comprises administering to the subject a therapeutically effective amount of at least one compound of the invention, which is optionally in a pharmaceutical composition. In certain embodiments, the method further comprises administering to the subject an additional therapeutic agent that treats or prevents diabetes.

In certain embodiments, the diabetes is type I and/or type II diabetes. In other embodiments, the subject is a mammal. In yet other embodiments, the mammal is a human.

The method further includes a method of increasing the cell membrane permeability of a molecule, wherein the molecule is selected from the group consisting of an oligonucleotide, oligodeoxynucleotide, small molecule (defined as having <2,000 amu) and polypeptide, the method comprising derivatizing the molecule to form a compound of formula (II). In certain embodiments, the compound of formula (II) is cleaved within the cell releasing the molecule. In other embodiments, the compound of formula (II) is cleaved within the cell releasing a derivative of the molecule that has essentially the same biological activity as the molecule itself.

Combination Therapies

The compounds useful within the methods of the invention may be used in combination with one or more additional therapeutic agents useful for treating diabetes. These additional therapeutic agents may comprise compounds that are commercially available or synthetically accessible to those skilled in the art. These additional therapeutic agents are known to treat, prevent, or reduce the symptoms of diabetes.

In non-limiting examples, the compounds useful within the invention may be used in combination with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, glycogen synthase kinase-3 inhibitors, glycogen phosphorylase inhibitors, anorexic agents and lipase inhibitors. It is further possible to combine them with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, glycogen synthase kinase-3 inhibitors and glycogen phosphorylase inhibitors; and it is possible to combine them with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors and renal glucose re-uptake inhibitors. Among these, particular non-limiting examples are insulin; gliclazide, glimepiride and glibenclamide which are sulfonylurea agents; nateglinide, repaglinide and mitiglinide which are meglitinides; pioglitazone and rosiglitazone which are glitazones, metformin, phenformin and buformin which are biguanides; and acarbose, voglibose and miglitol which are α-glucosidase inhibitors.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated, each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg, to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In sonic embodiments, a dose of a compound of the invention used in compositions described herein is less than about 10,000 or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or e may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the thrill of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should he a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods and Materials
Materials

Thioflavin T (ThT) was purchased from Acros Organics (Fair Lawn, N.J.), lipids [dioleoylphosphatidylglycerol (DOPG) and dioleoylphosphatidylcholine (DOPC)] from Avanti Polar Lipids, Inc. (Alabaster, Ala.), 96-well plates (black, w/flat bottom) from Greiner Bio-One (Monroe, N.C., USA), silica plates (w/UV254, aluminium backed, 200 micron) and silica gel (standard grade, particle size 40-63 micron, 230×400 mesh) from Sorbent Technologies (Atlanta, Ga., USA), dry solvents from Sigma Aldrich (St. Louis, Mich.) or VWR (Bridgeport, N.J., USA), 2,6-dichloro-3-nitropyridine, alkyl iodides, triethylamine (dry), 2-chloro-1-methylpyridinium iodide, tert-butyl bromoacetate, trifluoroacetic acid (TFA), and triethylsilane (TES) from Sigma Aldrich (St. Louis, Mich., USA) and islet amyloid polypeptide (IAPP) from Genscript (Piscataway, N.J., USA) and Elim Biopharmaceuticals (Hayward, Calif., USA). IAPP was repurified and handled in-house as follows: IAPP (~2 mg) was solubilized in 7 M guanidinium hydrochloride. The solution was filtered (0.2 micron) and transferred to C-18 spin column, washed twice with water (400 µL each) followed by 10% acetonitrile in water, 0.1% formic acid (v/v) and then eluted into 200 µL of 50% acetonitrile in water, 0.1% formic acid (v/v). The concentration of IAPP was calculated at 280 nm ($\varepsilon=1400$ $M^{-1} \cdot cm^{-1}$). The IAPP solution was divided into several aliquots (20-50 µL, 1-2 mM), lyophilized, and stored as a white solid at −80° C. A fresh stock solution of IAPP was prepared in water from lyophilized aliquots for each experiment, Alexa-594 labelled IAPP was prepared (Magzoub, et al., FASEB J. 2012, 26, 1228-1238).

Unilameller Vesicles

Unless otherwise stated, LUVs used in this work were prepared from a 1:1 mixture of DOPG/DOPC. The lyophilized mixture was hydrated in 100 mM KCl, 50 mM sodium phosphate, and pH 7.4 for 20 minutes. A 20 mg/mL solution of lipid in buffer was passed 21 times through a polycarbonate membrane (pore diameter=100 nm). The phospholipid content of the final material was measured using a total phosphorous assay (Chen, et al., Anal. Chem. 1956, 28, 1756-1758).

Kinetic Assay

Amyloid reactions were conducted in buffer containing liposome (630 µM lipid) and 20 µM ThT in a black 96-well plate. This was followed by addition of small molecule dissolved in DMSO (final DMSO concentration=0.5%, v/v). Fibre formation was initiated by addition of IAPP stock solution. The final volume in each well was 200 µL. Kinetics of fibrillation was monitored by ThT fluorescence (Ex 450 nm and Em 485 nm) using a FluoDia T70 fluorescence plate reader (Photon Technology International, Edison, N.J., USA). The data were blank subtracted and renormalized to the maximum intensity of reactions containing only IAPP. Each kinetic trace was fit to a sigmoidal form:

$$I = \frac{(b_2 + m_2 t) + (b_1 + m_1 t)e^{\frac{t50-t}{\tau}}}{1 + e^{\frac{t50-t}{\tau}}} \quad (1)$$

where I is the fluorescence intensity, t is time, and b, m, and τ are dependent fitting variables. All samples were rim at least in triplicate and error bars shown in the text represent ±one standard deviation.

Transmission Electron Microscopy

10 µM IAPP was incubated in buffer (100 mM KCl, 50 mM sodium phosphate, pH 7.4) with 630 µM LUVs in the presence and absence of IAPP:small molecule=1:1. Aliquots were incubated for 60 s on glow-discharged (25 mA and 30 s) carbon-coated 300-mesh copper grids. After drying, grids were negatively stained for 60 s with uranyl acetate (2%, w/v). Micrographs were taken on a Phillips Teenai 12 transmission electron microscope (Hillsboro, Oreg., USA) at 120 kV accelerating voltages. All conclusions drawn from images in this work include at least one repeat in which the sample identity was withheld from the investigator preparing and analysing images.

Isothermal Calorimetry Titration (ITC)

ITC experiments were conducted in a NANO-ITC (TA instruments, New Castle, Del., USA). Solutions of small molecules (100 µM in 1 mM KCl, 20 mM Tris, pH 7.4) was serially titrated (50 µL injections via rotary syringe) into an isothermal sample cell containing 10 µM IAPP (250 µL in 1 mM KCl, 20 mM Tris, pH 7.4) with a stirring speed of 300 rpm. 10 s injections were spread 240 s apart. The heat associated with each injection (oligoquinoline:IAPP) was extracted by integrating area under each curve using Nano-Analyze software (New Castle, Del., USA). The heat of small molecule binding to IAPP was corrected by subtracting heat of oligoquinoline injections into buffer. The final corrected heats were plotted as a function of molar ratio (oligoquinoline:IAPP) and fitted with a one binding site model.

Circular Dichroism

CD spectra were collected on AVIV MODEL 215 (AVIV Instruments, Inc. Lakewood, N.J., USA) for 25 µM IAPP mixed with 1200 µM LUVs in 100 mM KCl and 50 mM sodium phosphate at pH 7.4. The data was collected from 200 to 260 nm at 0.5 nm intervals with 10 s averaging time and an average of 4 repeats. The CD spectra in the presence of oligoquinolines were recorded as above except collecting from 200 to 500 nm at a stoichiometric ratio of 1:1 (oligoquinoline:IAPP).

Small Molecule Characterization

Final steps of small molecule purification was conducted by HPLC using a Varian ProStar with VYDAC reverse-phase columns (4.6×100 mm, 1 mL/min, analytical; 10×100 mm, 3 mL/min, semiprep.). The mobile phase was composed of A: 5% ACN, 95% $H_2O$, 0.1% TFA (v/v) and B: 95% ACN, 5% $H_2O$, and 0.08% TFA (v/v). The solution NMR spectra of small molecules were recorded on 400, 500, and 600 MHz Agilent spectrometers. The deuterated solvents used for O-tert butyl ester protected and deprotected (O—COOH) oligoquinolines were $CDCl_3$ and $(CD_3)_2SO$ respectively. Splitting patterns that were difficult to interpret, are indicated as multiplet (m) or broad (b). Mass spectra were obtained using either MALDI-TOF Voyager DE Pro (Yale University, CBIC center) or University of Illinois Mass Spec. Facility. High-resolution electrospray ionization mass spectra were obtained using the Waters Synapt G2-Si ESI MS mass spectrometer (Milford, Mass., USA).

Fluorescence Correlation Spectroscopy

FCS measurements were made on a laboratory-built instrument based around an inverted microscope using an Olympus IX71 microscope (Olmpus, Tokyo, Japan), as described previously in Middleton, et al., Effects of Curvature and Composition on α-Synuclein Binding to Lipid Vesicles (Biophys. J. 2010, 99, 2279-2288). Briefly, a continuous-emission 488-nm diode-pumped solid-state 50 mW laser was set to 5-20 mW output power and further adjusted with neutral density filters to 18 µW of power just prior to entering the microscope. Fluorescence was collected through the objective and separated from the excitation laser using a Z488rdc long-pass dichroic and an HQ600/200m bandpass filter (Chroma, Bellows Falls, Vt., USA). Fluorescence was focused onto the aperture of a 50 µm optical fibre coupled to an avalanche photodiode (Perkin Elmer, Waltham, Mass., USA). A digital correlator (Flex03LQ-12; Correlator.com, Bridgewater, N.J., USA) was used to generate autocorrelation curves.

Measurements were made in 8-well chambered coverglasses (Nunc, Rochester, N.Y., USA) which were plasma treated followed by precoating with polylysine-conjugated polyethylene glycol (PEG-PLL), to prevent ADM-116 and/or IAPP from adsorbing to chamber surfaces. Low density PEG coating was preformed by preparing a 100 mg/ml solution of PEG (MW=2 KDa, NANOCS, Boston, Mass., USA) in Poly-L-Lysine hydrobromide (Sigma Aldrich, St. Louis, Mich., USA). Reaction was preformed for 6 h in dark at room temperature, followed by overnight dialysis. Chambers were incubated overnight with PEG-PLL solution, rinsed thoroughly with Millipore water, and stored in water before use. All samples were incubated in buffer (20 mM Tris, pH 7.4, 10 mM NaCl) for 1 h prior to taking measurements. Titration was performed keeping constant concentrations of ADM-116$_F$ (25 nM) and adding increasing concentrations of IAPP. The autocorrelation curves were collected at regular intervals (10 min), and each autocorrelation curve was collected over 10 sand repeated 30 times.

Autocorrelation curves were fitting using Matlab (The MathWorks, Nattick, Mass., USA) and further global analysis were performed on IgorPro (ADInstruments, Colorado Springs, Colo., USA). For ADM-116, the model for a single diffusing species undergoing 3D Brownian diffusion with a triplet state is given by Eq. 2.

$$G(\tau) = \frac{1}{N(1-T)} \times \left(1 - T + Te^{(-t/\tau_{triplet})}\right) \times \left[1 + \frac{\tau}{\tau_{d,1}}\right]^{-1} \times \left[1 - \frac{\tau}{s^2\tau_{d,1}}\right]^{-\frac{1}{2}} \quad (2)$$

Here, N is the number of ADM-116$_F$ molecules in the detection volume, T is the fraction of molecules in the triplet state and $\tau_{triplet}$ is the triplet state relaxation time. The characteristic translational diffusion time of a diffusing particle is given by $\tau_{d,1}$.

In the presence of IAPP, the model for two-component analysis is given by:

$$G(\tau) = \frac{1}{N(1-T)} \times$$
$$\left(1 - T + Te^{(-t/\tau_{triplet})}\right) \times \left[r \times \left[1 + \frac{\tau}{\tau_{d,1}}\right]^{-1} \times \left[1 + \frac{\tau}{s^2\tau_{d,1}}\right]^{-\frac{1}{2}} + \right.$$
$$\left. (1-r) \times \left[1 + \frac{\tau}{\tau_{d,2}}\right]^{-1} \times \left[1 + \frac{\tau}{s^2\tau_{d,2}}\right]^{-\frac{1}{2}}\right] \quad (3)$$

where r is the fraction of the fast-diffusing component with a diffusion time $\tau_{d,1}$, whereas $\tau_{d,2}$ is the diffusion time of the slow component. The structure factor, s, was determined as a free parameter for solutions of free Alexa Fluor 488 hydrazide dye and then fixed to the experimentally determined value of 0.17 for all subsequent fittings. For experiments in the presence of IAPP, global analysis was performed by fixing the predetermined values for the diffusion coefficient, triplet diffusion time, and amplitude for ADM-116. The triplet state of IAPP bound and unbound ADM-116 were considered to be the same.

Confocal Microscopy

Images were obtained in 8 well. NUNC chambers (Thermo Scientific, Rochester, N.Y., USA) seeded with 20000-25000 cells/well. After culturing for 48 h, the medium was replaced with medium containing constituents according to the experiment performed. For time dependent localization experiments of IAPP, the medium contained 100 nM IAPP$_{594}$, 13 µM unlabelled peptide and incubated for the specified time points. For experiments in the presence of ADM-116$_F$ and ADM-3$_F$, additional fluorescein labelled and unlabelled small molecules, 200 nM and 13 µM, respectively was introduced in the medium. For delayed addition experiment with small molecules, the medium was removed for the second time, replacing with medium containing the small molecule. Images were acquired after 48 h total incubation time. Imaging was carried out at the Yale Department of Molecular, Cellular, and Developmental Biology imaging facility, on a Zeiss LSM 510 confocal microscope, using; a x63 Plan-Apo/1.4-NA oil-immersion objective with DIC capability (Carl Zeiss, Oberkochen, Germany). For all experiments reporting on the uptake of labelled IAPP, the gain setting for the red channel was kept constant from sample to sample. Image acquisition and processing were achieved using Zeiss Efficient Navigation (ZEN) and Image J software.

Imaging FRET (Forster Resonance Energy Transfer)

The INS-1 growth media was then replaced with media containing 100 nM $IAPP_{594}$ and incubated for 18 h. Media was then replaced a second time with media containing 200 nM $ADM-116_F$. Images were taken after 5 h incubation. Background FRET was determined using parallel experiments where 100 nM $IAPP_5$ was initially incubated for 18 h in cells in the presence of a further 13 µM of unlabelled IAPP. Media was then replaced with media containing 200 nM $ADM-116_F$. Imaging was carried out on a Zeiss LSM 510 confocal microscope, using a x100 Plan-Apo/1.4-NA oil-immersion objective with DIC capability (Carl Zeiss, Oberkochen, Germany). For $ADM-116_F$, fluorescein was excited with a 488 nm Argon2 laser and detected through a 505-550 nm emission filter. $IAPP_{594}$ was excited with a 561 Argon2 laser and detected through a 590-630 nm emission filter. For all experiments the pinhole was kept constant to the Z-slick thickness of each filter channel. Single cell images were obtain for donor alone, acceptor alone and donor-acceptor fusion channels. Image acquisition and processing were achieved using Zeiss Efficient Navigation (ZEN) and Image J software. The Image J plugin, RiFRET, was used to calculate and remove the bleed through for each channel and to calculate a pixel-based FRET efficiency. The FRET distance was then calculated using:

$$E = \frac{R_0^6}{R_0^6 + r^6} \quad (4)$$

Where E is the calculated efficiency of FRET energy transfer, $R_0$ is the Forster distance (60 Å for fluorescein-Alexa594 pair) and r is the distance between the donor and the acceptor.

Cell Culture

Rat insulinoma INS-1 cells (832/13, Dr. Gary W. Cline, Department of Internal Medicine, Yale University) were cultured at 37° C. and 5% $CO_2$ in phenol red free RPMI 1640 media supplemented with 10% fetal bovine serum, 1% penicillin/streptomycin (Life Technologies, Carlsbad, Calif., USA), and 2% INS-1 stock solution (500 mM HEPES, 100 mM L-glutamine, 100 mM sodium pyruvate, and 2.5 mM β-mercaptoethanol). Cells were passaged upon reaching 95% confluence (0.25% Trypsin-EDTA, Life Technologies), propagated, and/or used in experiments. Cells used in experiments were pelleted and resuspended in fresh media with no Trypsin-EDTA.

Giant Plasma Membrane Vesicle (GPMV) Isolation

GPMVs were isolated from INS-1 cells (Schlamadinger et al., Biophys. J. 2014, 107, 2559-2566, Kendhale et al., J. Org. Chem. 2011, 76, 195-200). Briefly, cells were plated in 35 mm dishes and cultured for 48 h. Cells were washed with a 10 mM HEPES, 150 mM NaCl, 2 mM $CaCl_2$ (pH=7.4) twice and were then exposed to 10 mM N-ethyl maleimide (NEM, Sigma Aldrich, St, Louis, Mich., USA) for 2 h. Collected samples were then passed over a gravity-flow column (Bio-Rad) containing size exclusion Sephacryl matrix of pore size 400-HR (Sigma Aldrich, St. Louis, Mich., USA) allowing the purification of GPMVs from residual cell debris.

GPMV Imaging

Images were obtained in 8 well NUNC chambers (Thermo Scientific, Rochester, N.Y., USA) including 250 µl of GMPV stock solution. For experiments in the presence of $ADM-116_F$ or $ADM-3_F$, 200 nM of small molecule was incubated in the GMPV solution for 24 h at room temperature. Imaging was carried out at the Yale Department of Molecular, Cellular, and Developmental Biology imaging facility, on a Zeiss LSM 510 confocal microscope, using a x63 Plan-Apo/1.4-NA oil-immersion objective with DIC capability (Carl Zeiss, Oberkochen, Germany). For all experiments, the gain setting for the green channel was kept constant from sample to sample. Image acquisition and processing were achieved using Zeiss Efficient Navigation (ZEN) and Image J software.

Cell Viability

Cell viability was measured colourimetrically using the Cell-Titer Blue (CTB, Promega, Madison, Wis., USA) fluorescence-based assay. Cells were plated at a density 5000 cells/well in 96-well plates (BD Biosciences, San Diego, Calif.). Peptide was directly introduced to each well after 48 h of culture and then further incubated for an additional 48 h. For time dependent experiments, cells were incubated with peptide for the specified time points. After the incubation period, 20 µL CTB reagent was added to each well and incubated at 37° C. and 5% $CO_2$ for 2.5-3.5 h. Fluorescence of the resorufin product was measured on a FluoDia T70 fluorescence plate reader (Photon Technology International, Birmingham, N.,.USA). All wells included the same amount of water to account for different concentrations of peptide added to sample wells. Wells that included water vehicle but not peptide served as the negative control (0% toxic), and wells containing 10% DMSO were the positive control (100% toxic). Percent toxicity was calculated using following equation:

$$\% \text{ Toxicity} = 100 - \left[100 \cdot \left(\frac{\langle S \rangle - \langle P \rangle}{\langle N \rangle - \langle P \rangle}\right)\right] \quad (5)$$

Each independent variable is the average of eight plate replicates from the negative control (<N>), positive control (<P>), and samples (<S>). Results presented for viability experiments are an average of three such experiments conducted independently on different days. Error bars represent the standard error of the mean.

Apoptosis was measured colourimetrically by detecting caspase 3/7 (Caspase-Glo® 3/7 Assay, Promega, Madison, Wis., USA). Cells were plated at a density 5000 cells/well in 96-well plates (BD Biosciences, San Diego, Calif., USA). Peptide was directly introduced to each well after 48 h of culture and then further incubated for the times specified in the main text. After the incubation period, 20 µL, Caspase-Glo® 3/7 reagent (containing a mixture of caspase-3/7 DEVD-aminoluciferin substrate and a proprietary thermostable luciferase in a reagent optimized for caspase-3/7 activity) was added to each well and incubated at 37° C. and 5% $CO_2$, for 2 h. Fluorescence of the free aminoluciferin product was measured on a FluoDia T70 fluorescence plate reader (Photon Technology International, Birmingham, N.J., USA). For protein concentration dependence measurements, carrier buffer was added as required to ensure identical volumes of protein were added to each well.

Example 1

Time Dependent Localization of IAPP

Figure 2:
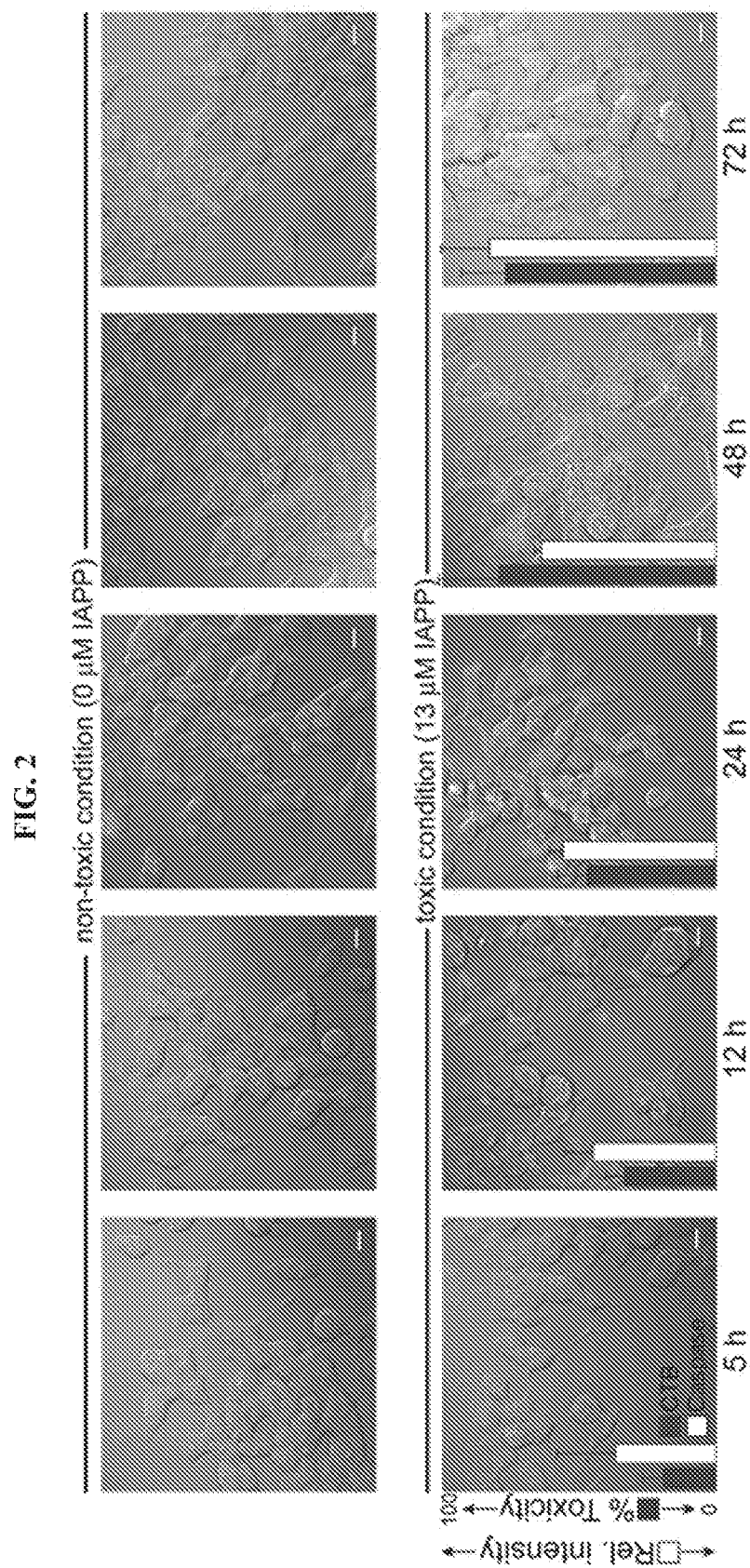
FIG. 2 comprises a series of images illustrating time dependent uptake of IAPP and toxicity. At time zero. 100 nM IAPP$_{A594}$ with (toxic) and without (non-toxic) an additional 13 μM of unlabelled IAPP was added to culture media of INS-1 cells. Confocal images were taken at the indicated time points. Scale bar=10 μm. Graphic inset: Colourimetric evaluation of toxicity (CTB) and apoptosis (Caspase) at the toxic condition relative to vehicle-only controls.

INS-1 cells were incubated with 100 nM IAPP labelled at its N-terminus with Alexa-594 (IAPP$_{A594}$). Co-addition of 0 µM or 13 µM unlabelled IAPP corresponds to non-toxic and toxic conditions respectively. At 5 h, under non-toxic conditions, IAPP was not significantly internalized (FIG. 2). By 12 h, intracellular IAPP was readily observed with maximum extent of internalization apparent at 24 h (FIG. 2). At all time-points under this non-toxic condition, IAPP appeared as diffuse puncta, possibly a consequence of energy dependent cellular uptake under these conditions. Under toxic conditions, slightly elevated uptake of IAPP was apparent by 5 h. By 12 h, contrasting behaviour could be clearly seen with the toxic condition showing external and internalized puncta and larger assemblies. By 24 h, extracellular IAPP was a small fraction of the total IAPP. At 48 h, large intracellular aggregates appeared and continued to increase in intensity through 72 h. This progression suggests that aggregation was mediated by the intracellular environment, consistent with work showing culture media and plasma membrane to be inhibitory to amyloid formation.

In certain embodiments, cytotoxicity is mediated by intracellular IAPP. The time dependence of IAPP-mediated toxicity was measured in parallel to imaging. Apoptosis was apparent as early as 5 h with caspase 3/7 activity continuing to increase over the course of observation (FIG. 2). The fraction of cells affected by IAPP could be approximated by monitoring total cytosolic reductase activity relative to IAPP-free controls. The trend clearly parallels the apoptosis. Importantly, continued increases in apoptotic activity were apparent long after the 24 h time-point where little extracellular IAPP was evident (FIG. 2). Taken together, this suggests the site of toxicity is intracellular. Without wishing to be limited by any theory, small molecule modulation of IAPP requires a compound that can be internalized.

Example 2

Targeting Membrane Bound IAPP

Figure 3A:
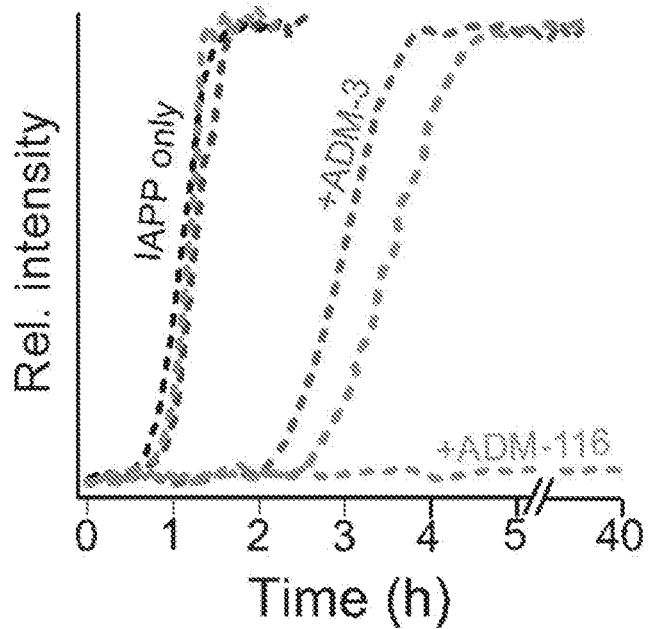
FIGS. 3A-3B illustrate effects of ligands on the kinetics of IAPP fibre formation.
Figure 9A:
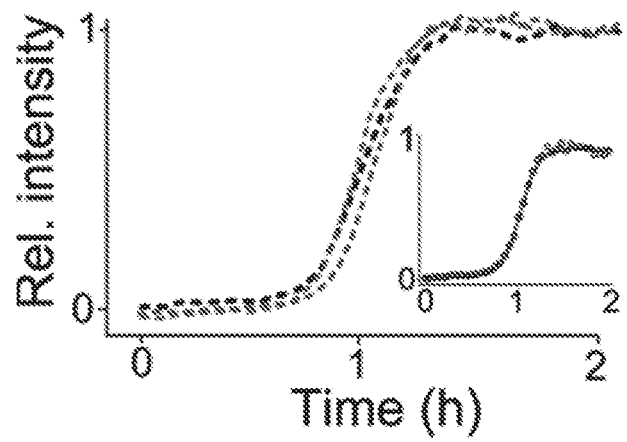
FIGS. 9A-9B illustrate kinetic profiles of IAPP self-assembly.
Figure 9B:
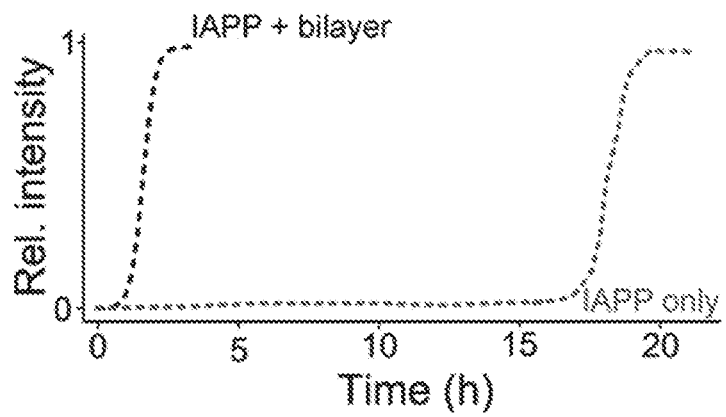

There is a direct correlation between targeting membrane bound IAPP, inhibition of several solution-based gains-of-function, and cytotoxic rescue. Without wishing to be limited by any theory, compounds that target intracellular IAPP may be more likely to be found among membrane active inhibitors of IAPP self-assembly. In solution, assembly of 10 µM IAPP into fibres occurred with a reaction midpoint, t$_{50}$, of 18±1.4 h (FIG. 9). The same reaction conducted in the presence of large unilamellar vesicles (LUVs) was accelerated to a t$_{50}$ of 1.1±0.1 h (FIG. 3A). The latter serves as a reference condition under which small molecules can be assessed for activity in the context of a bilayer.

Figure 3B:
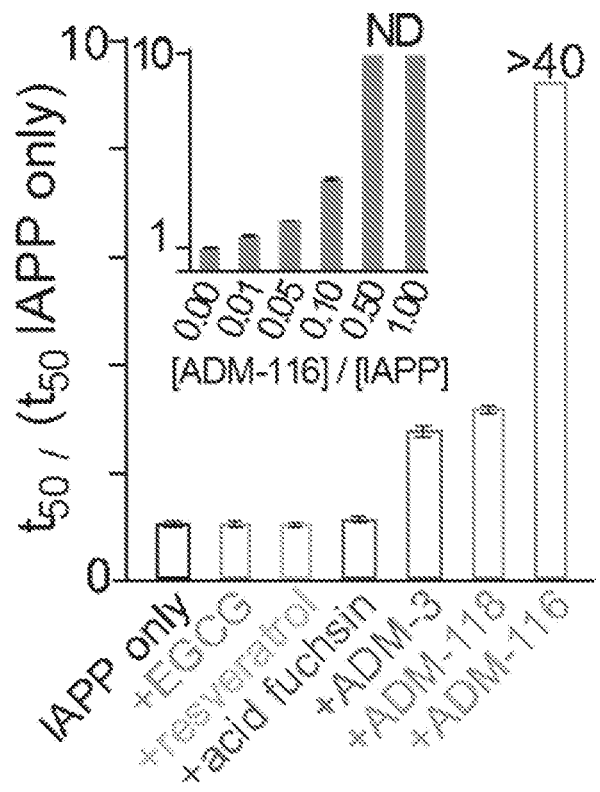
Figure 5A:
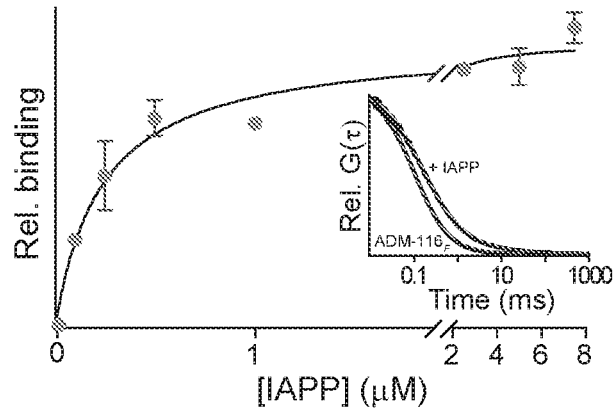
FIGS. 5A-5D illustrate small molecules binding to IAPP and their structural effects.
Figure 5B:
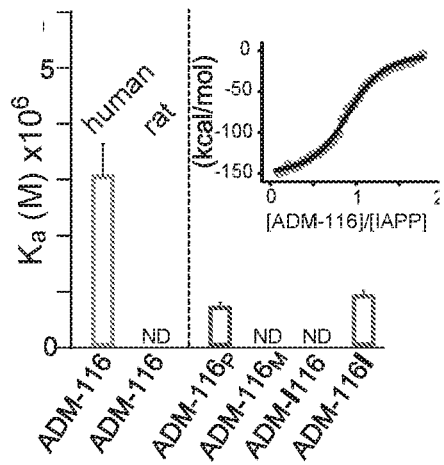
Figure 5C:
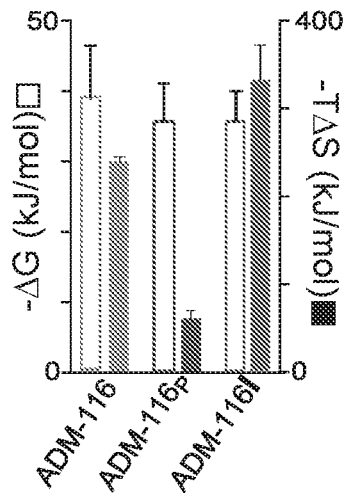
Figure 5D:
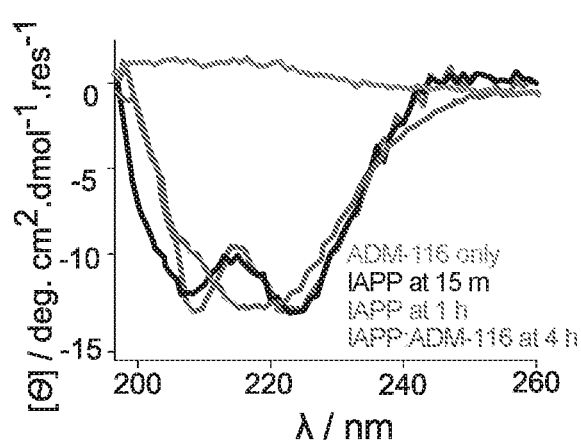
Figure 10A:
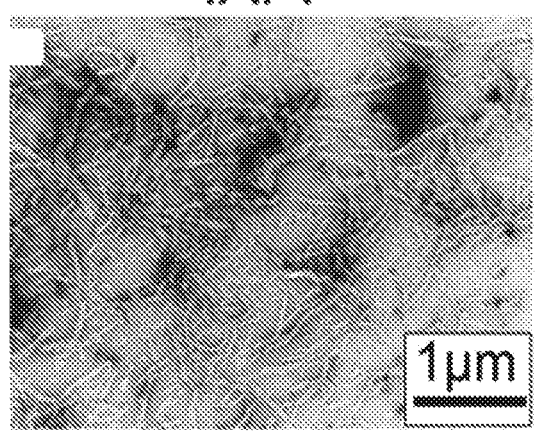
FIGS. 10A-10B illustrate images of ADM-116 inhibited assembly.
Figure 10B:
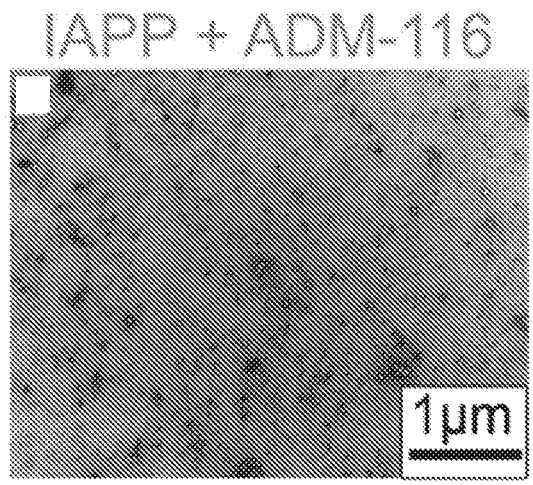

ADM-116 (FIGS. 1A-1B) is a small molecule with marked activity in LUV catalysed fibrillation assays. At 1:1 (IAPP:ADM-116), liposome catalysed fibrillation was undetectable (a t$_{50}$ >40 fold higher than control) with significant inhibition observable even at 1:0.1 (FIG. 3). Amyloid formation was not observed by electron microscopy (FIG. 10) and far-UV CD (FIG. 5D). In comparison, compounds ADM-3 (FIG. 15) and ADM-118 inhibit by factors of 2.7±0.1 and 3.3±0.1 fold respectively. Other natural product compounds such as EGCG, acid fuchsin (AF) and resveratrol, show no detectable effect (FIG. 3). In certain embodiments, ADM-116 contained functional moieties, the steric and physico-chemical properties of which result in exceptional inhibition of lipid catalysed amyloid assembly.

Figure 11:
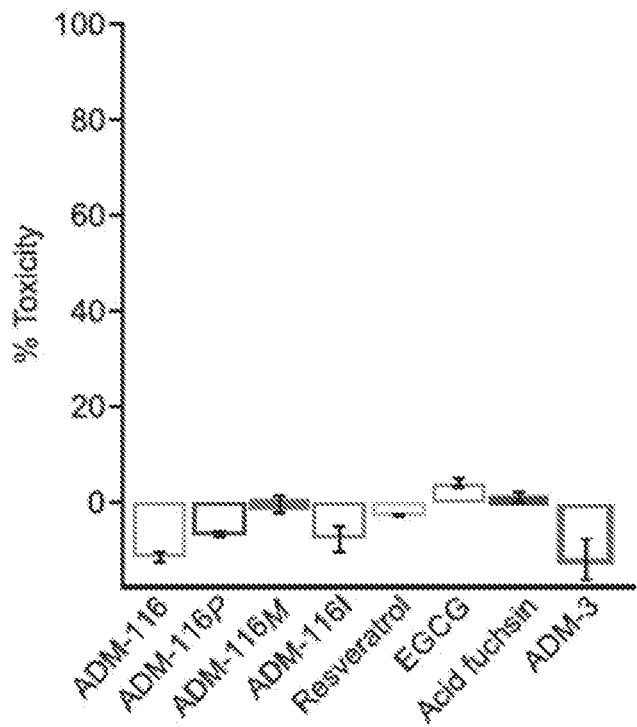
FIG. 11 illustrates intrinsic toxicity of selected small molecules. INS-1 cells were incubated with 13 μM of each of the indicated small molecules. Viability was assayed after 48 h using Cell-Titer Blue (CTB) and compared to carrier-only controls. Error bars represent the standard deviation in the mean of four replicates.

ADM-116 rescued IAPP induced toxicity. After 48 h of incubation with 13 µM IAPP, INS-1 viability was decreased 78±8%. Co-addition of ADM-116 at a stoichiometric ratio of 1:1 (IAPP:ligand) wholly restored viability (FIGS. 4A-4B). The compound ADM-3, a tripyridylamide, was also active on membrane bound IAPP and also restored cell viability (FIG. 4A) with a dose dependence comparable to ADM-116 (FIG. 4B). Resveratrol, EGCG and acid fuchsin were ineffective in rescuing toxicity under same conditions. The origin for this disparity was the requirement for IAPP and these small molecules to be preincubated for >11 h prior to adding the complexes to cell culture. In contrast, IAPP and the small molecule were co-introduced to cell culture. At concentrations investigated herein, none of the molecules showed intrinsic toxicity towards INS-1 cells, nor interfered with the colourimetric assay (FIG. 11).

ADM-116, but not ADM-3, rescued cells from intracellular IAPP toxicity. In light of the intracellular origins of toxicity suggested elsewhere herein (FIG. 2), cell viability was instead assessed under conditions in which introduction of IAPP was followed by a delay prior to the addition of small molecule. Remarkably, even after a delay of 24 h, ADM-116 was capable of rescuing IAPP induced cytotoxicity by 47±4%. In marked contrast, ADM-3 was ineffective in rescuing toxicity when added after 12 h (FIG. 4C). As IAPP was internalized by 24 h of incubation (FIG. 2), this suggests that the mechanism of ADM-116 rescue includes penetration of the plasma membrane.

Example 3

Molecular Specificity of Binding

The solution and cellular activities of ADM-116 were enabled by formation of a discrete complex with IAPP. Unlabelled IAPP was titrated into a solution of 25 nM fluorescein labelled ADM-116 (ADM-116$_F$) and the diffusion time of the small molecule in the absence and presence of peptide was monitored by fluorescence correlation spectroscopy (FCS). ADM-116$_F$ alone shows a $\tau_D$ of 130±13 µs (FIG. 5a). Upon titration with IAPP, a second component was evident with a diffusion time of $\tau_D$=~400 µs. The consistency of the diffusion time over the course of the titration indicates a discrete complex. Fitting the fractional amplitude of bound to unbound ADM-116$_F$ gave K$_d$ of 240±60 nM. The $\tau_D$ of fluorescently labelled IAPP alone was 230±4 µs. Assuming all components are spheres, diffusion scales by mass. The stoichiometry of the complex under this assumption was 1:1. Isothermal titration calorimetry (ITC) using unlabelled IAPP and ADM-116 yielded an exothermic profile that clearly fitted a one site binding model with a K$_a$=3.1±0.6×10$^6$M$^{-1}$ (K$_d$=320±60 nM) (FIG. 5b and Table 1). Thus, ADM-116 formed a discrete complex with strong affinity to IAPP.

TABLE 1

Binding Affinities. ITC-derived thermodynamic parameters for the binding of the indicated ligands with IAPP. Units of energy are kJ/mol. Presented errors are the standard deviation from experiments performed at least three times.

| Compound | $K_a \times 10^{-6}$ | n | ΔH | ΔS | TΔS | ΔG |
|---|---|---|---|---|---|---|
| ADM-116 | 3.1 ± 0.6 | 1.0 ± 0.1 | −230 ± 5 | 750 ± 17 | −220 ± 5 | −36 ± 7 |
| ADM-116| | 0.7 ± 0.1 | 0.9 ± 0.1 | −89 ± 8 | 190 ± 29 | −57 ± 9 | −33 ± 3 |
| ADM-116$_P$ | 0.9 ± 0.1 | 1.0 ± 0.0 | −340 ± 36 | −1000 ± 120 | −310 ± 36 | −33 ± 4 |

Figure 12:
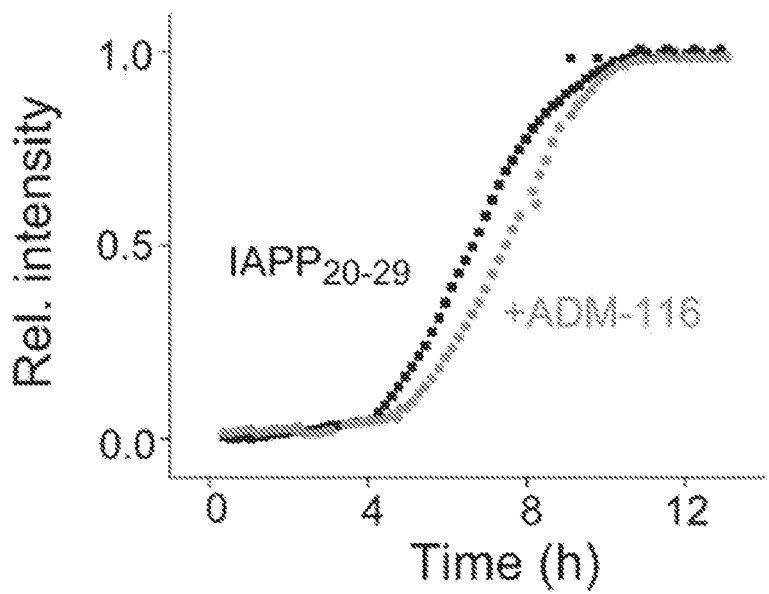
FIG. 12 illustrates effects of ADM-116 on the assembly kinetics of IAPP$_{20-29}$. Representative kinetic profile of amyloid assembly by 200 μM of the 10-residue peptide, IAPP$_{20-79}$. Reactions are shown in the absence and presence of 200 μM ADM-116 at equimolar ratio.
Figure 14:
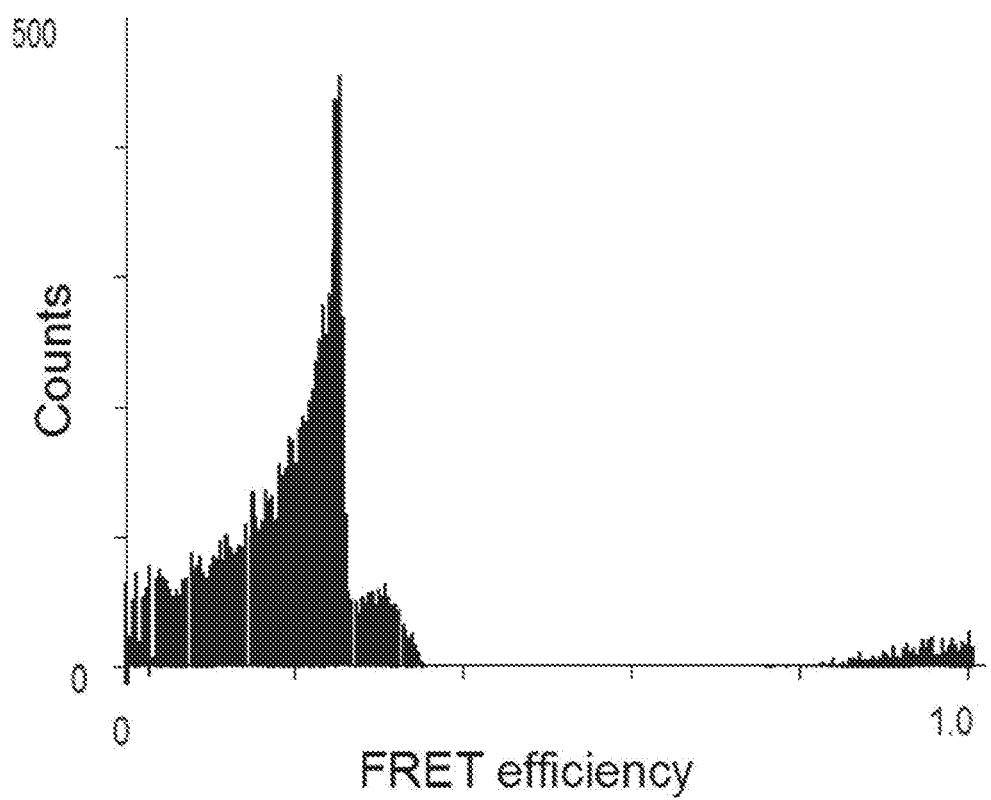
FIG. 14 illustrates determination of background Förster resonance energy transfer (FRET) in confocal imaging. Confocal imaging and processing for FRET was conducted in a manner matched to that used in the FIGS. 7A-7D. Preparation of the cells was also matched, except that the 100 nM IAPP$_{594}$ was augmented with 13 μM unlabelled IAPP to dilute out any possibility of structure-specific FRET taking place.

ADM-116 stabilized the α-helical sub-domain of IAPP. The far-UV CD spectrum of membrane bound IAPP exhibited two minima near 208 and 222 nm, characteristic of α-helical structure (FIG. 5D). This profile transitioned to that of β-sheet, characteristic of amyloid, within 1 h. In contrast, IAPP remained predominantly α-helical even after 4 h when incubated with ADM-116 (1:0.5, IAPP:ADM-116). α-helical structure within the membrane binding sub-domain of IAPP is mapped to segments containing most of the first 22 residues of IAPP. Within this stretch, the sequence variant of IAPP from rat, rIAPP, varies only at position 18 (H18R). Binding of ADM-116 by rIAPP was not detectable (FIG. 5B). An additional five residues differ between hIAPP and rIAPP over residues 23-29. Amyloid nucleation in full length hIAPP was mediated, in part, by residues 20-29. The kinetic profile of amyloid formation by 200 μM of the 10-residue sub-peptide, IAPP$_{20-29}$, gave a t$_{50}$ of 6.6±0.3 h (FIG. 12). The presence of 1:1 ADM-116 has little effect on the independent amyloid assembly of IAPP$_{20-29}$. Thus, ADM-116 did not functionally interact with human residues 20-29, nor does it detectably bind to rIAPP. Combined with the observation of membrane bound α-helical stabilization, this suggests that ADM-116 binds to the α-helical subdomain of IAPP.

Example 4

Specificity of Intracellular Binding

Figures 6A, 6B, 6C:
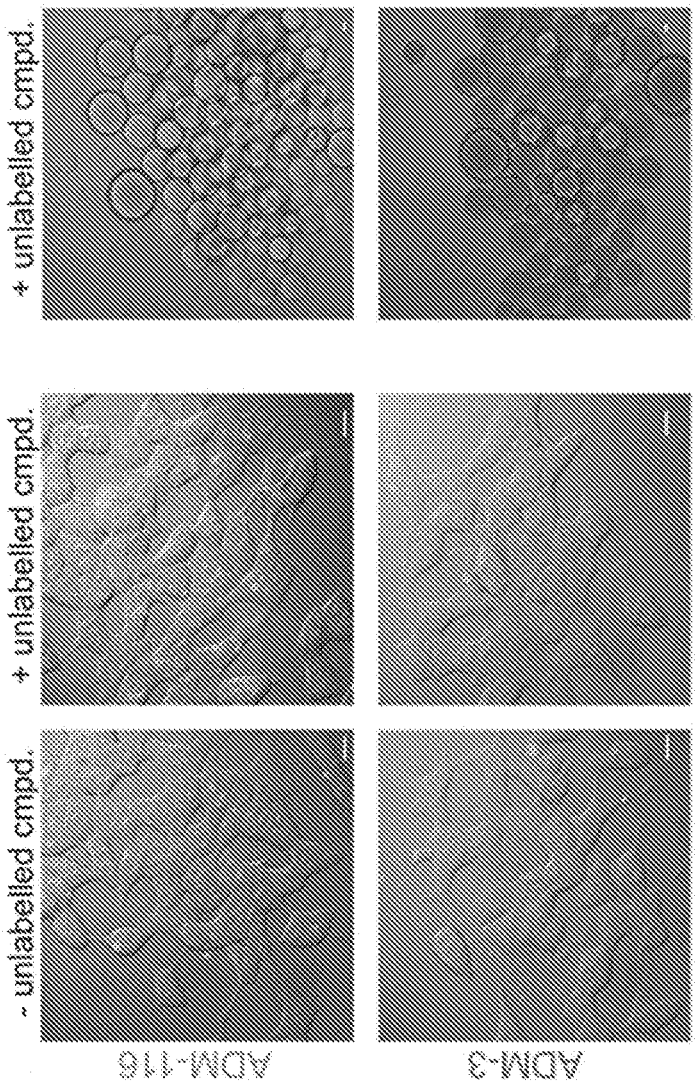
FIGS. 6A-6C illustrate membrane translocation and partitioning.

To gain mechanistic insight, ADM-116 was fluorescently labelled at its OCH$_3$ end, applied to INS-cells and visualized by confocal microscopy. Fluorescein labelled ADM-116 (ADM-116$_F$), at non-rescue (200 nM) and rescuing (200 nM+15 μM ADM-116) concentrations, was able to penetrate the cell membrane (FIG. 6A). In contrast, fluorescein labelled ADM-3 (ADM-3$_F$) showed no capacity to populate the cell interior (FIG. 6A). Giant plasma membrane derived vesicles (GPMVs) were then prepared from live INS-1 cells. ADM-116, and not ADM-3, showed a clear capacity to penetrate the GPMVs (FIG. 6B) indicating that not only does the former small molecule cross the membrane, it does so without assistance from active cellular processes.

Cellular rescue was associated with colocalization of protein and small molecule. INS-1 cells were treated with toxic concentrations of IAPP (100 nM IAPP$_{594}$ and 13 μM IAPP). After 20 h, rescuing concentrations of ADM-116 (200 nM ADM-116$_F$ and 15 μM ADM-116) were added. In rescued cells, IAPP colocalized with ADM-116 and fewer IAPP aggregates were observed (FIG. 7A). An alternative mechanism operated under conditions in which IAPP and ADM-116 were cointroduced. Although IAPP and ADM-116 could separately enter cells (FIG. 2, and FIG. 6A), added together, they colocalized on the cell surface (FIG. 7B). A similar observation can be made for ADM-3 (FIG. 13). This suggests that the interaction of ADM-116 or ADM-3 with IAPP prohibited the entry of toxic peptide into the cells. In contrast, rescue by delayed addition of ADM-116 appeared to disrupt toxic aggregate formation by direct interaction.

Intracellular rescue was a consequence of direct interactions between IAPP and ADM-116. Förster resonance energy transfer (FRET) measurements were made in live cells. Here, 200 nM ADM-116$_F$ was applied to INS-1 cells 20 h after 100 nM IAPP$_{594}$. Looking only to data above background, nonradiative energy transfer from ADM-116 to IAPP$_{594}$ was readily apparent and intracellular (FIG. 7C). Importantly, statistical assessment of the FRET revealed a Gaussian distribution strongly consistent with interactions not only being close (~40 Å), but also discrete and therefore specific (FIG. 7D).

Example 5

Structure, Dynamics and Function of ADM-116

ADM-116 is a folded molecule with a hydrophobic core. For FDA approved drugs, measured and calculated octanol-water partition coefficients are closely comparable (FIG. 6C). The predicted and experimental log P for ADM-3 are −0.7 and −2.0, consistent with its practical solubility in buffer (FIG. 6C). For ADM-116 however, there is a 7-order of magnitude disparity. The calculated log P was 7.6 (comparable to cholesterol) while the measured log P was 0.6. This anomaly may be a consequence of the folded nature of ADM-116. Overall, ADM-116 is anionic (−2), water soluble and yet capable of passive cell membrane penetration. This suggests a paradigm for cell penetration in which the folding/refolding of the small molecule is central to this process.

Refolding of ADM-116 is affected by IAPP binding. Refolding permits oligoquinolines to sample an equal mixture of right-(P) and left-(M) mirror-image helices. The CD spectrum of ADM-116 in aqueous buffer contained equal contributions from these two hands resulting in a flat line at 390 nm (FIG. 8B). In marked contrast, the CD spectra of ADM-116 recorded in the presence of stoichiometric IAPP (FIG. 8A) showed positive ellipticity. Binding clearly shifted the refolding equilibrium between right and left handed helical states.

Figure 15:
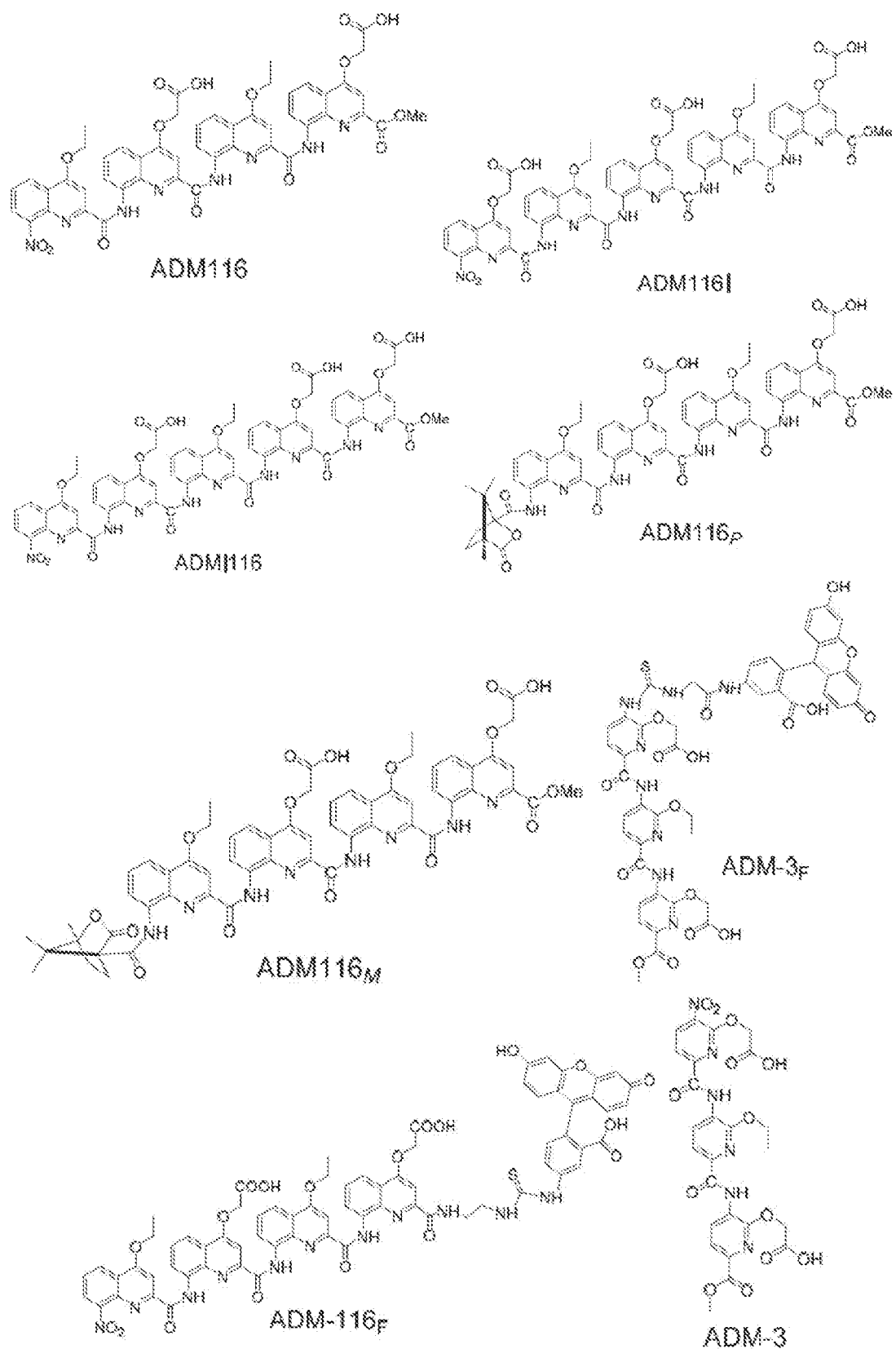
FIG. 15 illustrates the chemical structures of the small molecules: ADM116, ADM-116I, ADM-I116, ADM-116$_P$, ADM-116$_M$, ADM-3$_F$, ADM-3, and ADM-116$_F$.
Figure 16A:
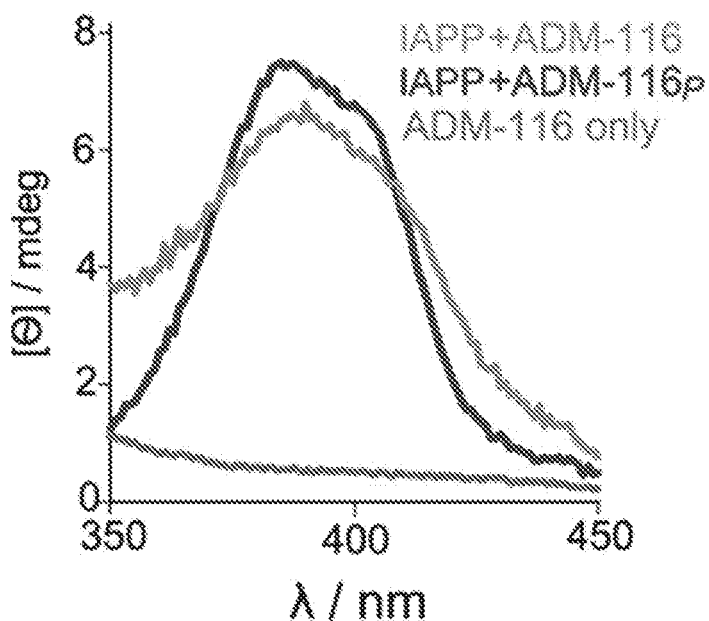
FIGS. 16A-16B illustrate the conformational changes induced by ADM-116.

IAPP binds preferentially to the (P) conformer of ADM-116. Two analogues were synthesized in which chiral camphenyl groups were coupled to the NO$_2$ terminus of ADM-116 (FIG. 15). CD spectra confirm the induction of helical bias (FIG. 8B) with ADM-116$_P$ and ADM-116$_M$ defined as the derivatives that give positive and negative profiles at 390 nm respectively. For neither compound could the ratio of right/left hand helical states he determined in absolute terms. Importantly, the intensity of ADM-116 in the presence of IAPP was within 90% that of ADM-116$_P$ (FIG. 8A and FIG. 16). By ITC, the K$_a$ of IAPP to ADM-116$_P$ is 0.9±0.1×10$^6$ M$^{-1}$; within a factor of three of ADM-116. In contrast, binding was not detectable for ADM-116$_M$ (FIG. 5B). This pattern was evident in diverse assays. For lipid catalysed fibrillation reactions, ADM-116$_P$ was as potent an inhibitor as ADM-116 while ADM-116$_M$ inhibited fibrillation only weakly (FIG. 8C). In cell toxicity assays, ADM-116$_P$ showed 2.4 times greater inhibition of toxicity than ADM- $116_M$ (FIG. 8C). Thus, in two solution biophysical assays and in toxic rescue, IAPP:ADM-116 interactions were stereospecific.

Figure 16B:
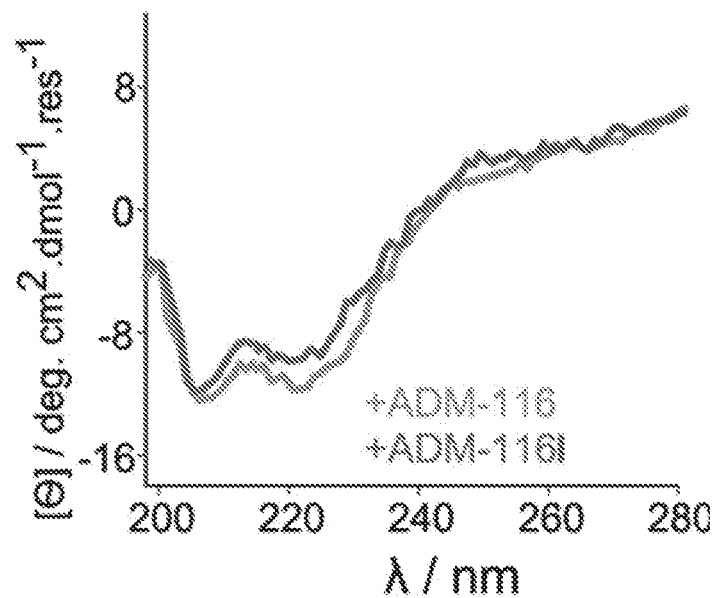

IAPP binding to ADM-116 included interactions with the OCH$_3$ end of the ADM-116 helix. Enantiomeric interconversion in oligoquinolines is more restricted with increasing length. Here, two molecules were synthesized in which ADM-116 was lengthened by one subunit either at the NO$_2$ (ADM-116I), or OCH$_3$ end (ADM-I116). The lateral surfaces of ADM-116I and ADM-I116 necessarily included the surface of ADM-116. If IAPP:ADM-116 binding includes contact with the ends of the quinoline helix, then binding to one of the two variants should be more strongly affected. The K$_a$ of IAPP:ADM-116I was similar to ADM-116 (K$_a$=7±1×10$^6$M$^{-1}$). This binding induced a random coil to α-helix transition comparable to ADM-116 (FIG. 16B). The binder, ADM-116$_P$, was also an NO$_2$ end derivative. In marked contrast, no binding is detected for ADM-I116. This indicates that IAPP interacted with the OCH$_3$ end of ADM-116.

Intracellular toxic rescue by ADM-116 was dependent on oligoquinoline length. In toxicity studies, the co-addition of ADM-116I and IAPP resulted in diminished toxicity relative to IAPP alone (FIG. 4A). However, if ADM-116I was added to INS-1 cells after IAPP was internalized, rescue was no longer observed (FIG. 4C). In other words, the addition of a fifth quinoline to ADM-116 resulted in a molecule that retained activities comparable to ADM-3, i.e. a compound that is an effective antagonist provided IAPP and small molecule encounter each other in the extracellular environment.

Without wishing to be limited to any theory, differences in the behaviour of ADM-116I and ADM-116 could be mapped to changes in the relative folded stability of the small molecule. The ΔΔG of IAPP binding to ADM-116I versus ADM-116 was ~3 kJ/mol (FIG. 5C and Table 1). Changes to entropic contributions (ΔTΔS) were ~160 kJ/mol (FIG. 5C). If the IAPP:ADM-116I and IAPP:ADM-116 interfaces are structurally the same, this disparity must instead be mapped to differences in the unbound state(s) of the oligoquinolines. The large entropic contribution resembles a hydrophobic effect; consistent with the expectation that the tetraquinoline, ADM-116, more readily samples unfolded states than pentaquinoline, ADM-116I. The fact that the tetraquinoline, ADM-116$_P$, has a thermodynamic profile more similar to ADM-116 complements this assertion. Structural assessment of the IAPP:ADM-116I complex by CD showed weak ellipticity at 390 nm compared to IAPP:ADM-116 even after days of incubation (FIG. 8A). Thus, whereas binding affinity of IAPP to ADM-116I is comparable to ADM-116, the capacity of the binding energy to shift the enantiomeric equilibrium is reduced. Taken together, these observations suggest that ADM-116 exists predominantly in its folded state, but readily samples partially and fully unfolded states.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

---

What is claimed is:

1. A compound of formula (I), or a salt, solvate, or N-oxide thereof, and any combinations thereof:

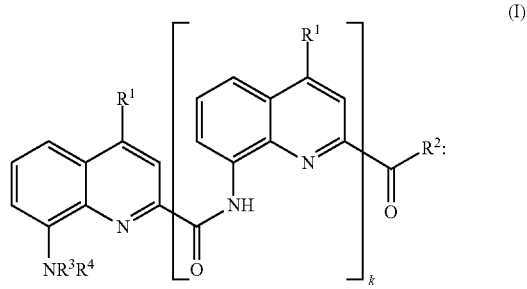

(I)

wherein each occurrence of R$^1$ is independently selected from the group consisting of —OH, —O(C$_1$-C$_6$)alkyl, —O(C$_1$-C$_6$)haloalkyl, —O(CH$_2$)$_m$C(=O)OR$^5$, —OC(=O)R$^5$, —NH$_2$, —SH, —SO$_3$H and —OPO(OH)$_2$;

wherein R² is selected from the group consisting of —(C₁-C₆)alkyl, —(C₁-C₆)heteroalkyl, —OR⁵, —(C₃-C₁₀)heterocyclyl, aryl and heteroaryl, wherein the alkyl, hetereoalkyl, heterocyclyl, aryl or heteroaryl group is optionally substituted;

wherein R³ and R⁴ are independently selected from the group consisting of H, —(C=O)₀₋₁(C₁-C₆)alkyl, —(C=O)₀₋₁(C₃-C₈)cycloalkyl, —(C=O)₀₋₁(C₁-C₆)heteroalkyl, —(C=O)₀₋₁aryl, and —(C=O)₀₋₁heteroaryl, wherein the alkyl, cycloalkyl, aryl or heteroaryl group is optionally substituted; or R³ and R⁴, together with the nitrogen to which R³ and R⁴ are connected, form —(C₃-C₁₀)heterocyclyl or —NO₂;

wherein each occurrence of R⁵ is independently selected from the group consisting of H, —(C₁-C₆)alkyl, —(C₁-C₆)heteroalkyl, —(C₃-C₈)cycloalkyl, —(C₄-C₁₀)heterocyclyl, aryl, and —(C₅-C₁₀)heteroaryl, wherein the alkyl, heteroalkyl, cycloalkyl, heterocyclyl, aryl, or heteroaryl group is optionally substituted;

wherein each occurrence of m is independently an integer ranging from 1 to 5;

wherein k is an integer ranging from 1 to 5;

wherein the compound of formula (I) has a net negative charge at physiological pH; and wherein any two quinoline groups that are covalently linked to each other do not have the same R¹ substituent.

2. The compound of claim 1, wherein at least one occurrence of R¹ is selected from the group consisting of —O(CH₂)ₘC(=O)OH, —SO₃H and —PO(OH)₂.

3. The compound of claim 1, wherein at least two occurrences of R¹ are independently selected from the group consisting of —O(CH₂)ₘC(=O)OH, —SO₃H and —PO(OH)₂.

4. The compound of claim 1, wherein every other quinoline group in (I) has a R¹ independently selected from the group consisting of —O(CH₂)ₘC(=O)OH, —SO₃H and —PO(OH)₂.

5. The compound of claim 4, wherein, if a given quinoline group in (I) has a R¹ selected from the group consisting of —O(CH₂)ₘC(=O)OH, —SO₃H and —PO(OH)₂, the quinoline groups to which the given quinoline group is covalently linked have R¹ substituents that are independently selected from the group consisting of —OH, —O(C₁-C₆)alkyl, —O(C₁-C₆)haloalkyl, —OC(=O)R⁵, —NH₂, and —SH, and wherein R⁵ is not H.

6. The compound of claim 1, wherein each occurrence of R¹ is independently selected from the group consisting of —OCH₂CH₃ and —OCH₂COOH; NR³R⁴ is —NO₂; R² is —OMe; and k is 3 or 4.

7. The compound of claim 1, which is the compound of formula (III) or (IV):

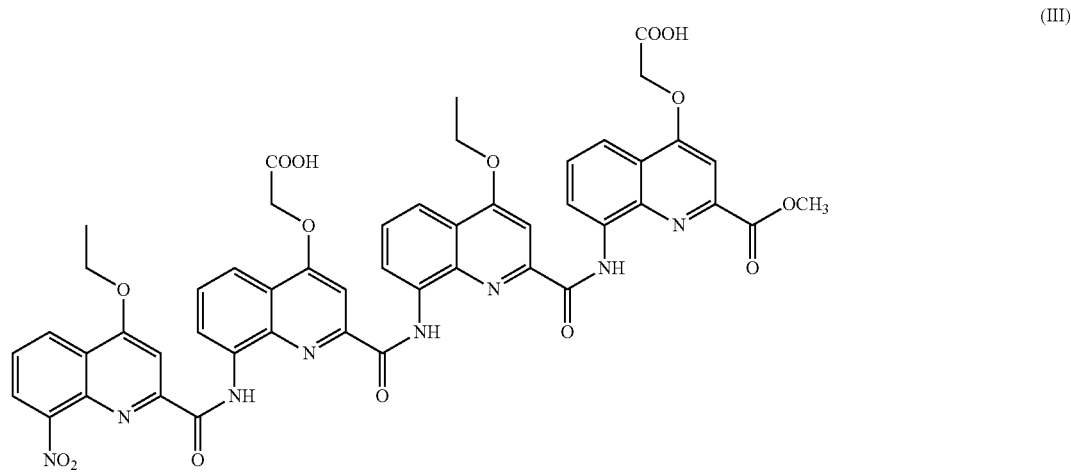

(III)

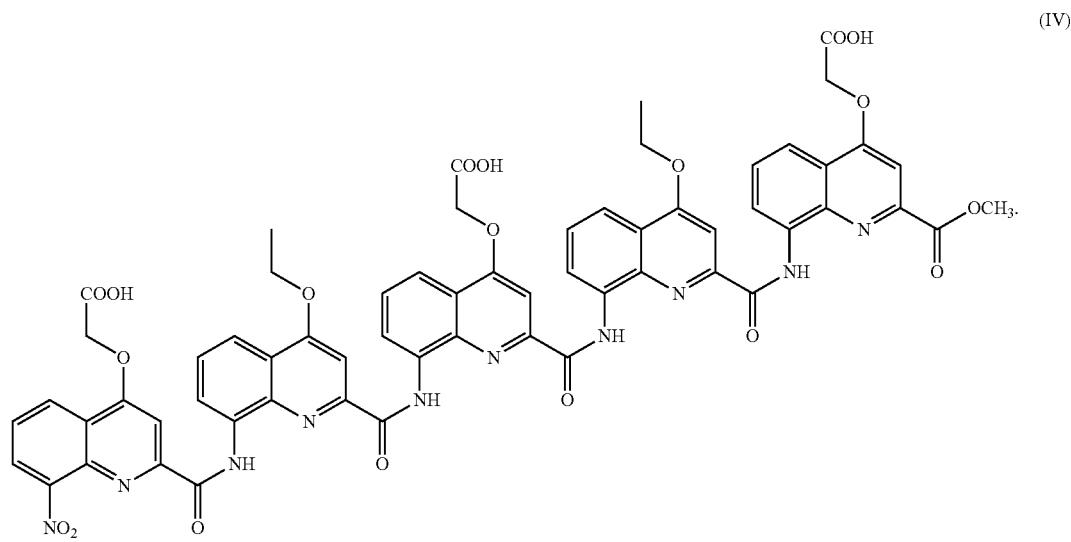

(IV)

8. The compound of claim 1, wherein at physiological pH the compound of formula (I) has a net negative charge that is selected from the group consisting of −1, −2, −3, −4, −5, and −6.

9. The compound of claim 1, wherein the compound is further coupled with a detectable label.

10. A pharmaceutical composition comprising at least one compound of claim 1 and at least one pharmaceutically acceptable carrier.

11. The pharmaceutical composition of claim 10, further comprising at least one additional therapeutic agent.

12. The compound of claim 1, wherein k is 1.
13. The compound of claim 1, wherein k is 2.
14. The compound of claim 1, wherein k is 3.
15. The compound of claim 1, wherein k is 4.
16. The compound of claim 1, wherein k is 5.
17. The compound of claim 1, wherein the compound is water soluble.
18. The compound of claim 1, wherein the compound is capable of passively penetrating a cell membrane.
19. The compound of claim 9, wherein the detectable label is selected from the group consisting of a radioisotope, stable isotope, fluorophore, electron dense metals, biotin, DNA, RNA, antibody epitope, spin label, reactive peptide tag, quantum dot, and any combinations thereof.

* * * * *